US011260043B2

(12) United States Patent
McAllister et al.

(10) Patent No.: US 11,260,043 B2
(45) Date of Patent: *Mar. 1, 2022

(54) METHODS AND COMPOSITIONS FOR TREATING CANCER

(71) Applicant: Sutter Bay Hospitals, San Francisco, CA (US)

(72) Inventors: Sean D. McAllister, San Francisco, CA (US); Pierre-Yves Desprez, Richmond, CA (US)

(73) Assignee: SUTTER BAY HOSPITALS, San Francisco, CA (US)

( * ) Notice: Subject to any disclaimer, the term of this patent is extended or adjusted under 35 U.S.C. 154(b) by 1843 days.

This patent is subject to a terminal disclaimer.

(21) Appl. No.: 14/587,831

(22) Filed: Dec. 31, 2014

(65) Prior Publication Data

US 2015/0150844 A1 Jun. 4, 2015

Related U.S. Application Data

(63) Continuation of application No. 14/075,848, filed on Nov. 8, 2013, which is a continuation of application No. 12/600,553, filed as application No. PCT/US2008/063837 on May 16, 2008, now Pat. No. 9,084,771.

(60) Provisional application No. 60/988,071, filed on Nov. 14, 2007, provisional application No. 60/938,635, filed on May 17, 2007.

(51) Int. Cl.
| | | |
|---|---|---|
| *A61K 36/00* | (2006.01) | |
| *A61K 31/352* | (2006.01) | |
| *A61K 31/35* | (2006.01) | |
| *A61K 31/05* | (2006.01) | |
| *A61K 45/06* | (2006.01) | |

(52) U.S. Cl.
CPC .......... *A61K 31/352* (2013.01); *A61K 31/05* (2013.01); *A61K 31/35* (2013.01); *A61K 45/06* (2013.01)

(58) Field of Classification Search
CPC .................................... A61K 36/00
USPC ........................................ 424/725
See application file for complete search history.

(56) References Cited

U.S. PATENT DOCUMENTS

| | | | |
|---|---|---|---|
| 6,946,150 B2 | 9/2005 | Whittle | |
| 7,968,594 B2 | 6/2011 | Guy et al. | |
| 8,632,825 B2 | 1/2014 | Velasco Diez et al. | |
| 2002/0137064 A1 | 9/2002 | Desprez et al. | |
| 2003/0021752 A1 | 1/2003 | Whittle et al. | |
| 2003/0158191 A1 | 8/2003 | Travis | |
| 2004/0039048 A1* | 2/2004 | Guzman Pastor et al. | 514/454 |
| 2004/0138293 A1 | 7/2004 | Werner et al. | |
| 2005/0165259 A1 | 7/2005 | Martin et al. | |
| 2006/0234273 A1 | 10/2006 | Desprez et al. | |
| 2006/0247304 A1 | 11/2006 | Guy et al. | |
| 2007/0072938 A1 | 3/2007 | Rose | |
| 2008/0057117 A1 | 3/2008 | Werner et al. | |
| 2008/0262099 A1 | 10/2008 | Whittle et al. | |
| 2010/0317729 A1 | 12/2010 | Guy et al. | |
| 2011/0086113 A1 | 4/2011 | Velasco Diez et al. | |
| 2011/0117216 A1 | 5/2011 | Velasco Diez et al. | |
| 2012/0225136 A1 | 9/2012 | Whittle et al. | |

FOREIGN PATENT DOCUMENTS

| | | |
|---|---|---|
| CN | 1976690 A | 6/2007 |
| EP | 1177790 A1 | 2/2002 |
| EP | 1802274 B1 | 9/2008 |
| EP | 2386322 A2 | 11/2011 |
| GB | 2380129 A | 4/2003 |
| GB | 2418612 A | 4/2006 |
| GB | 2448535 A | 10/2008 |
| GB | 2471987 A | 1/2011 |
| WO | 0158445 A1 | 8/2001 |
| WO | 0187295 A1 | 11/2001 |
| WO | 02069993 A1 | 12/2002 |
| WO | 2004041269 A2 | 5/2004 |
| WO | 2005120478 A1 | 12/2005 |
| WO | 2006107903 A2 | 10/2006 |
| WO | 2008144475 A1 | 11/2008 |

OTHER PUBLICATIONS

Tallarida, Genes & Cancer, vol. 2, No. 11, 2011, pp. 1003-1008.*
Hans-Georg Breitinger (2012). Drug Synergy—Mechanisms and Methods of Analysis, Toxicity and Drug Testing, Prof. Bill Acree (Ed.), ISBN: 978-953-51-0004-1, InTech, Available from: http://www.intechopen.com/books/toxicity-and-drug-testing/drug-synergy-mechanisms-and-methods-ofanalysis.*
Ben-Shabat et al., J. Med. Chem. 2006, vol. 49, pp. 1113-1117.
Guzman, Manuel, "Cannabinoids: Potential Cancer Agents." Nature Reviews Cancer, Oct. 2003, pp. 745-755, vol. 3.
Ligresti et al., Neuropharmacology, 2004, vol. 47, pp. 315-323.
Massi et al., The J. of Pharmacology and Experimental Therapeutics, 2004, vol. 308, No. 3, pp. 838-845.
Nickitas-Etienne, Athina, International Preliminary Report on Patentability and Written Opinion, dated Nov. 17, 2009, International Application Number: PCT/US08/63837.
Strasser et al., J. Clin. Oncol., Jul. 20, 2006, vol. 24, No. 21, pp. 3394-3400.
Tucker et al., Res. Commun. Chem. Pathol. Pharmacol. 1977, vol. 17, No. 4, pp. 703-714.
Velasco et al., Neuropharmacology, 2004, vol. 47, pp. 315-323.
Kogan et al., "Synthesis and Antitumor Activity of Quinonoid Derivatives of Cannabinoids", J. Med.Chem., 2004, 47, 3800-3806.
Adalpe et al., "Models of malignant glioma", Drug Discovery Today: Disease Models. 2006; 3(2): 191-6.

(Continued)

*Primary Examiner* — Michael V Meller
(74) *Attorney, Agent, or Firm* — Gavrilovich, Dodd & Lindsey LLP

(57) ABSTRACT

This disclosure provides compositions and method useful for treating cell proliferative disorders including cancer. The disclosure provides cannabidiol derivatives and compositions thereof either alone or in combination with THC or a derivative thereof.

2 Claims, 9 Drawing Sheets

Specification includes a Sequence Listing.

(56) References Cited

OTHER PUBLICATIONS

Blazquez, C. et al., "Inhibition of tumor angiogenesis by cannabinoids," Faseb J. 2003; 17: 529-531.
Blow, "Cell migration: our protruding knowledge", Nat Meth. 2007; 4: 589-94.
Boyden, "The chemotactic effect of mixtures of antibody and antigen on polymorphonuclear leucocytes", J Exp Med. Mar. 1, 1962; 115: 453-66.
Casanova, M.L. et al., "Inhibition of skin tumor growth and angiogenesis in vivo by activation cannabinoid receptors," J. Clinical Investigation. Jan 1, 2003; 111(1): 43-50.
Galve-Roperh I. et al., "Anti-tumoral action of cannabinoids: involvement of sustained ceramide accumulation and extracellular signal-regulated kinase activation," Nature Medicine. Mar. 2000; 6(3): 313-319.
Gilbert et al., A phase II study of temozolomide in patients with newly diagnosed supratentorial malignant glioma before radiation therapy. Neuro Oncol. Oct. 2002; 4(4): 261-7.
Grotenhermen F., "Pharmacokinetics and Pharmacodynamics of Cannabinoids," Clin Pharmacokinet. 2003; 42(4): 327-60.
Huang et al., "ECRG2 inhibits cancer cell migration, invasion and metastasis through the down-regulation of uPA/plasmin activity", Carcinogenesis. Nov. 2007; 28(11): 2274-81. Epub Jun 29. 2007.
Hulkower et al., "Cell migration and invasion assays as tools for drug discovery", Pharmaceutics. 2011; 3: 107-24.
Jacobsson et al., "Serum-Dependent effects of tamoxifen and cannabinoids upon C6 glioma cell viability", Biochem. Pharmacol., Dec. 15, 2000; 60(12): 1807-13.
Jacobsson, S.O.P. et al., "Inhibition of rat C6 glioma cell proliferation by endogenous and synthetic cannabinoids. Relative involvement of cannabinoid and vanilloid receptors", J. Pharmacology and Expt. Therapeutics, 2001; 299(3): 951-959.
Killestein et al., Safety, tolerability, and efficacy of orally administered cannabinoids in MS. Neurology. May 14, 2002; 58(9): 1404-7.
Levy, J.A. et al., "Modulation of the metastatic frequency of a murine mammary adenocarcinoma by a synthetic cannabinoid drug," Proceedings of the American Association for Cancer Research. 1979; 20: 624.
McAllister and Desprez. McAllister and Desprez Declaration. Molecular Mechanisms of Cannbinoid Antitumor Activity. Grant Proposal. Forbes Norris/MDA ALS Research Center. Award notice date Apr. 5, 2005.
McAllister and Desprez. McAllister and Desprez Declaration. Excel data reporting results of experiments. Nov. 26, 2012.
McAllister and Desprez. McAllister and desprez Declaration. Soroceanu et al., the role of ID-1 in modulating brain tumor invasion and dispersal. Neuro-oncology. 2009; 11: 564. Abstract #3.
Nurmikko et al., "Sativex successfully treats neuropathic pain characterised by allodynia: a randomised, double-blind, placebo-controlled clinical trial", Pain. Dec. 15, 2007; 133(1-3): 210-20. Epub Nov. 7, 2007.
Portella, Giuseppe et al., "Inhibitory effects of cannabinoid CB1 receptor stimulation on tumor growth and metastatic spreading: actions on signals involved in angiogenesis and metastasis," The FASEB Journal: Official Publication of the Federation of American Societies for Experimental Biology; Sep. 2003; 17(12): 1771-1773.
Robins et al., "Phase 2 trial of radiation plus high-dose tamoxifen tor gliblastoma multiforme: RTOG protocol BR-0021", Neuro Oncol, Jan. 2006; 8(1): 47-52.
Russo et al., A tale of two cannabinoids: the therapeutic rationale for combining tetrahydrocannabinol and cannabidiol. Med Hypotheses. 2006;66(2): 234-46. Epub Oct. 4. 2005.
Tucker et al., "Effects of cannabinoids on L1210 murine leukemia. 1. Inhibition of DNA synthesis", Res Commun Chem Pathol Pharmacol. Aug. 1977; 17(4): 703-14. Abstract.
The United Kingdom Parliament, Select Committee on Science and Technology Ninth Report (1998) at http://www.parliament.the-stationery-office.co.uk/pa/ld199798/ldselect/ldsctech/151/15101.htm.
The United Kingdom Parliament, Select Committee on Science and Technology Second Report (Mar. 14, 2001) at http://www.publicatians.parliament.uk/pa/ld200001/ldselect/ldsctech/50/5001.htm.
Vacanni et al., Cannabidiol inhibits human glioma cell migration through a cannabinoid receptor-independent mechanism. Br J Pharmacol. Apr. 2005; 144(8): 1032-6.

* cited by examiner

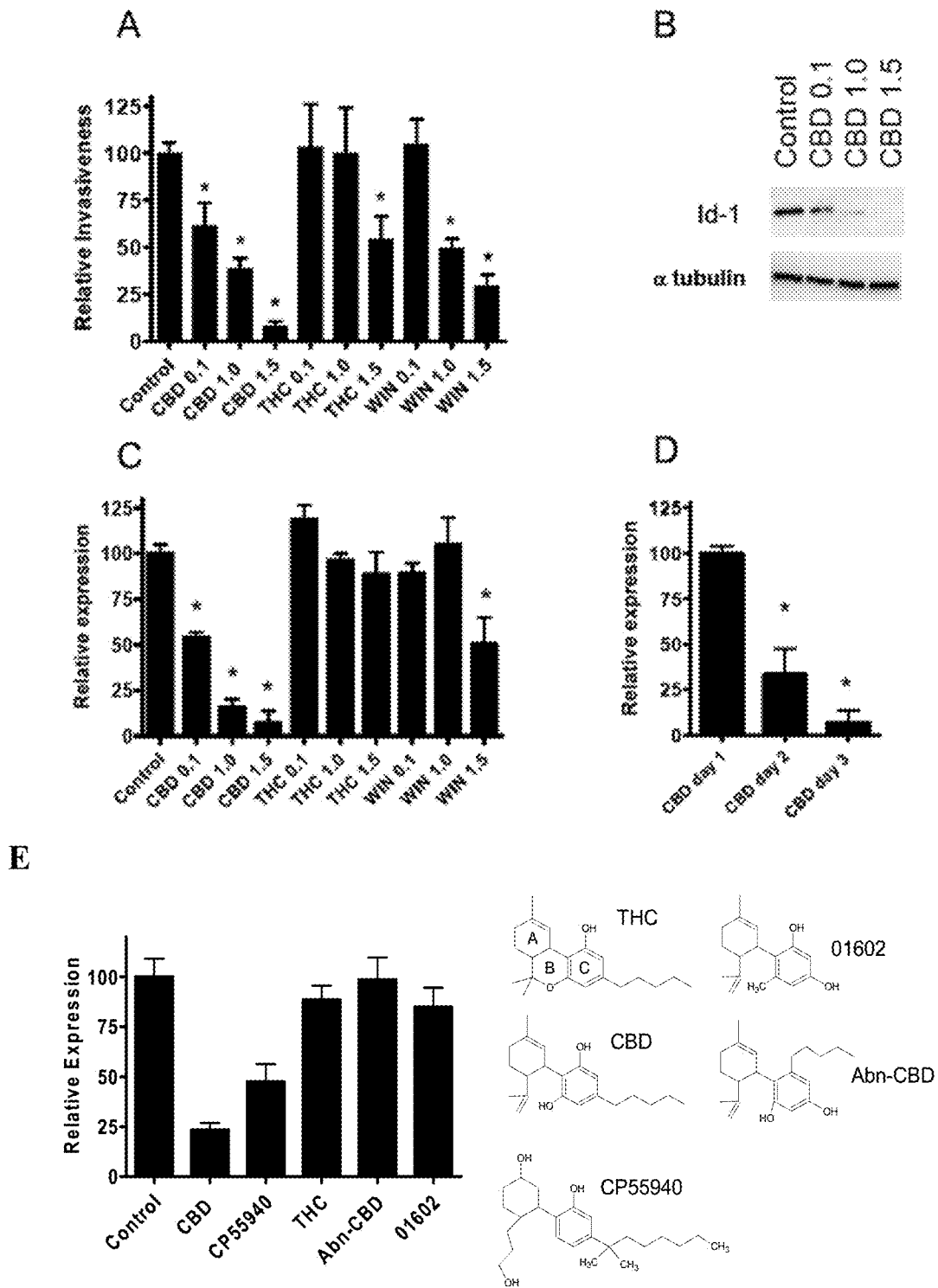
FIGURE 1A-E

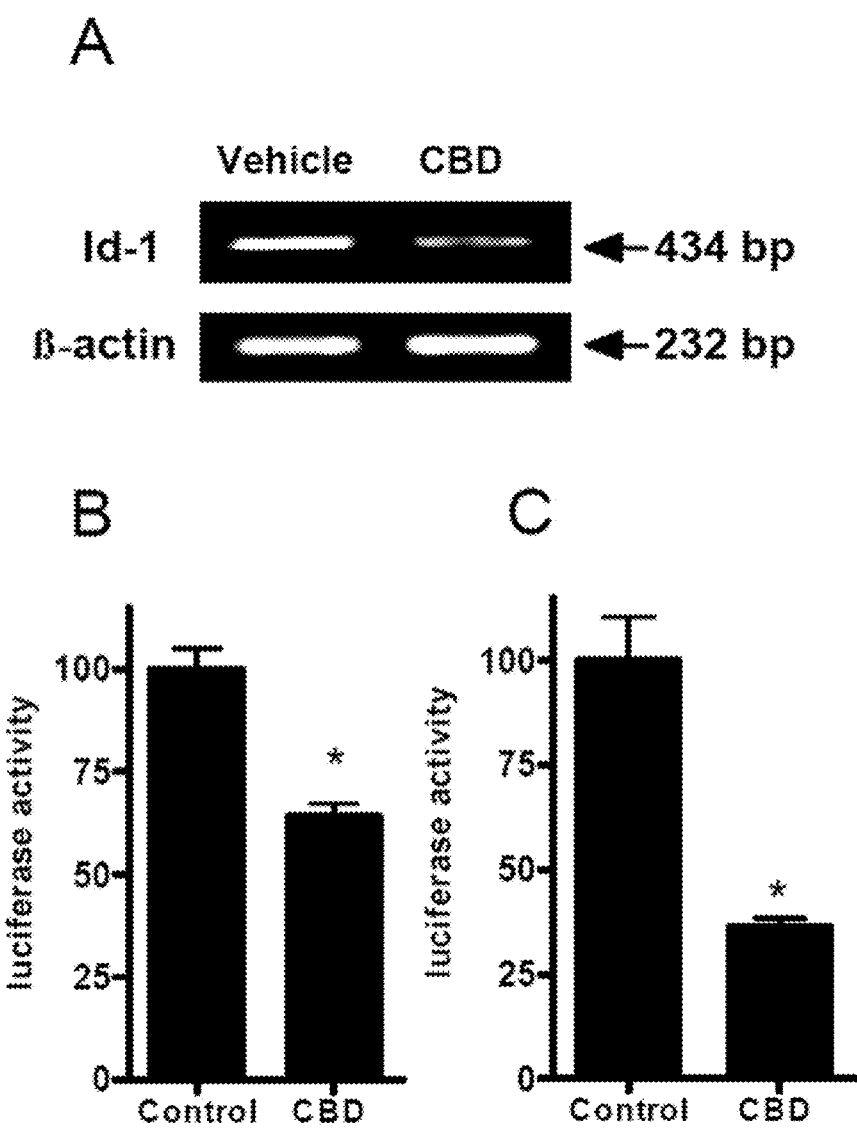
FIGURE 2A-C

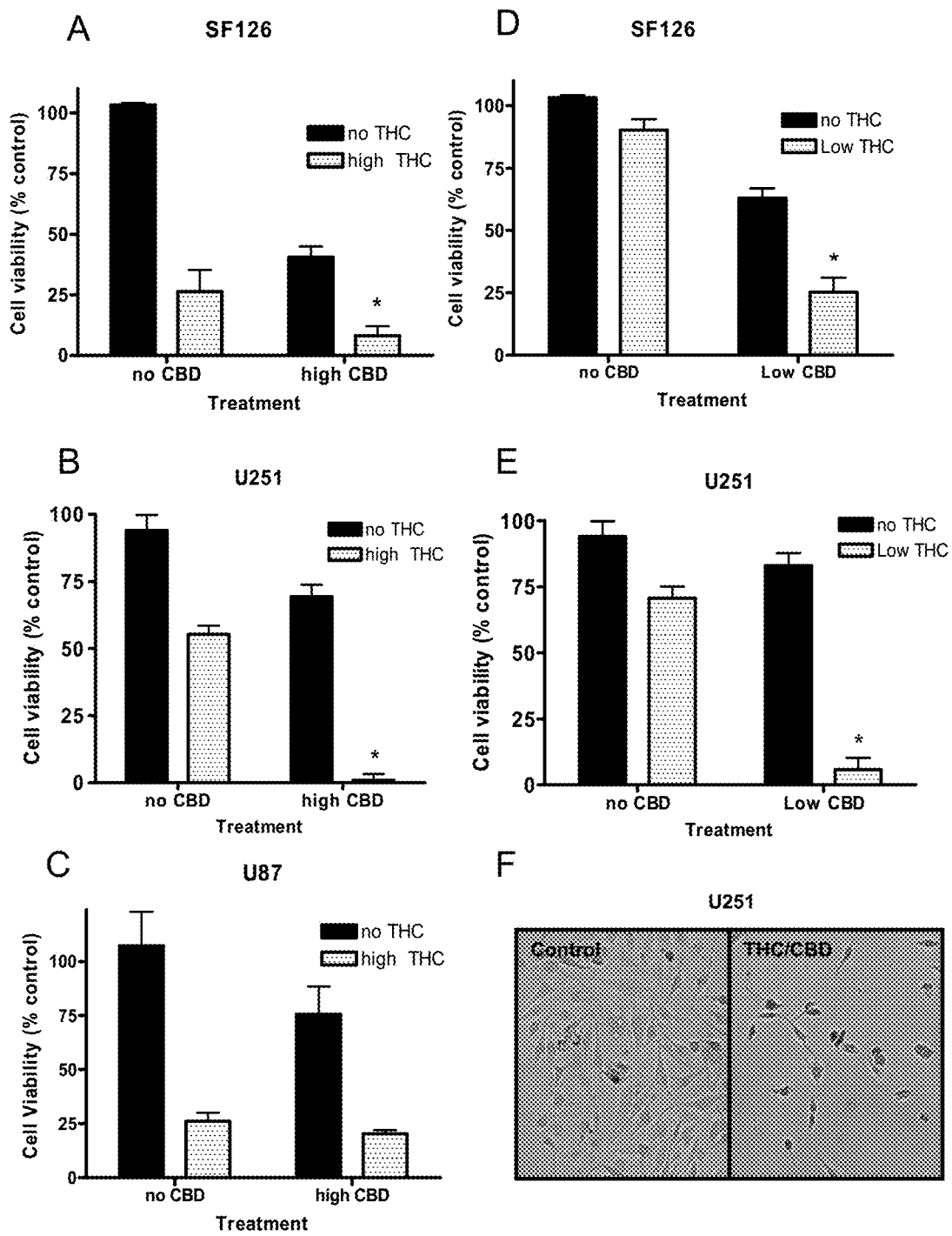
FIGURE 3A-F

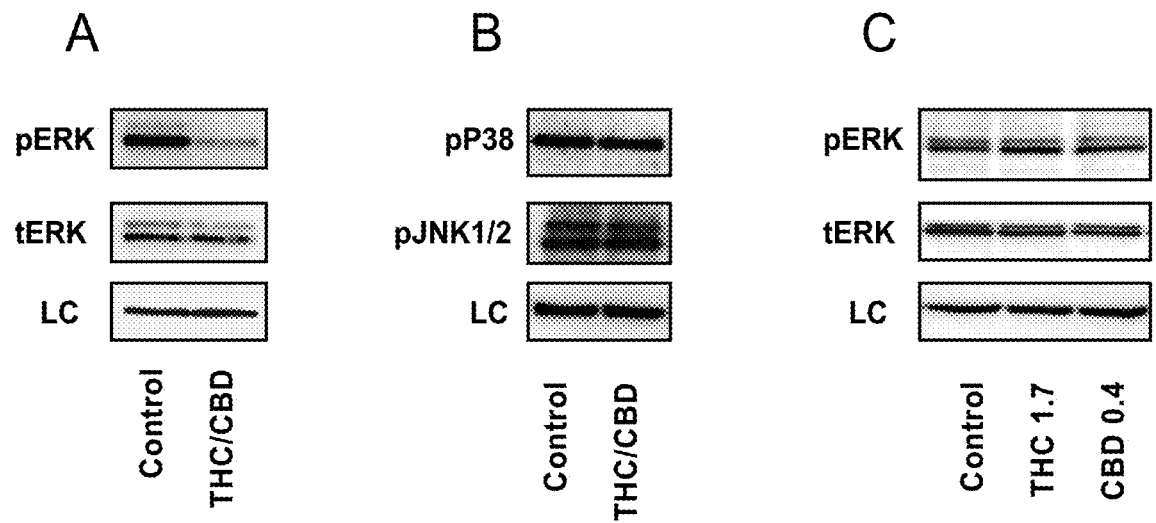
FIGURE 4A-C
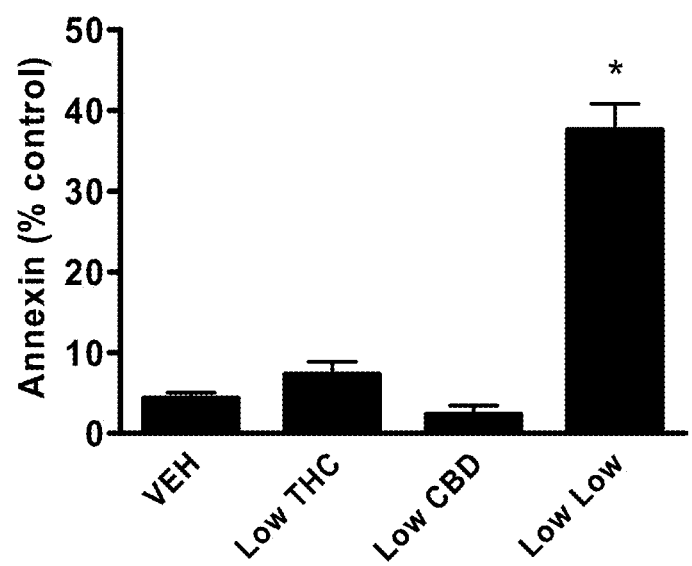
FIGURE 5

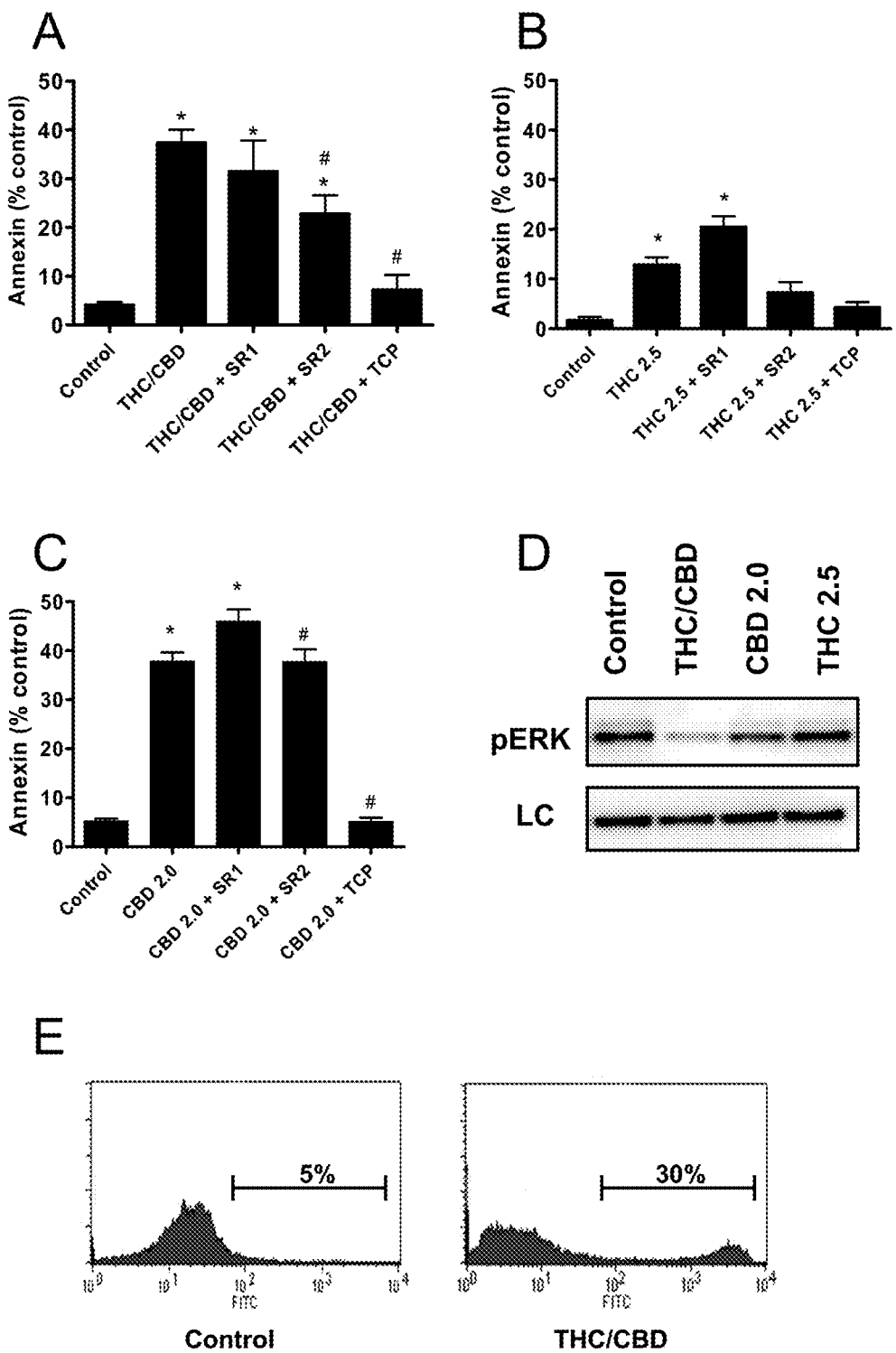
FIGURE 6A-E

A
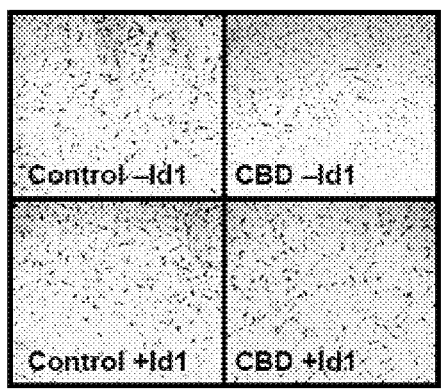
B
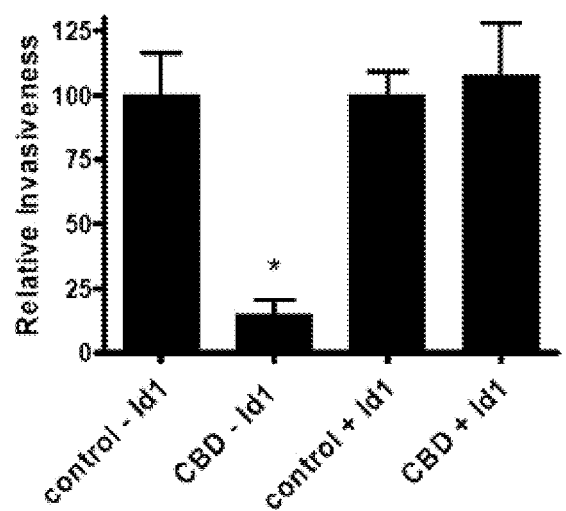
C
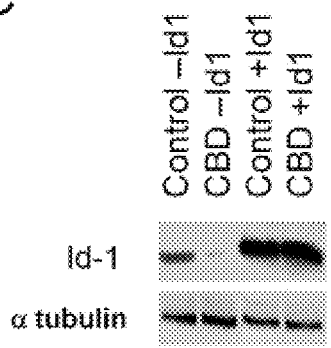
FIGURE 7A-C

METHODS AND COMPOSITIONS FOR TREATING CANCER

CROSS REFERENCE TO RELATED APPLICATIONS

This application is a continuation of U.S. application Ser. No. 14/075,848, filed Nov. 8, 2013, which is a continuation of U.S. application Ser. No. 12/600,553, having a filing date of Apr. 26, 2010, which is a U.S. National Stage Application filed under 35 U.S.C. § 371 and claims priority to International Application No. PCT/US08/63837, filed May 16, 2008, which application claims priority to U.S. Provisional Application Ser. Nos. 60/938,635, filed May 17, 2007, and 60/988,071, filed Nov. 14, 2007, the disclosures of which are incorporated herein by reference.

STATEMENT REGARDING FEDERALLY SPONSORED RESEARCH

This invention was funded by Grant Nos. CA102412 and CA82548 awarded by National Institutes of Health. The government has certain rights in the invention.

TECHNICAL FIELD

This invention relates to methods and compositions for treating cancer. More particularly, the invention provides cannabidiol derivatives and compositions thereof.

BACKGROUND

The hemp plant *Cannabis sativa*, commonly referred to as marijuana, has been used to alleviate symptoms of disease for thousands of years. Currently an oral formulation of $\Delta^9$-THC, the primary active cannabinoid constituent of marijuana, is approved as an antiemetic agent for cancer patients undergoing chemotherapy (Grinspoon, 1993). Additionally, studies suggest that cannabinoids may increase appetite and alleviate pain in the same patient population.

SUMMARY

The disclosure provides a method of treating cancer in a subject, comprising administering to a subject in need of such treatment a therapeutically effective amount of a composition comprising an agent that modulates the expression and/or activity of an Id helix-loop-helix polypeptide. In one embodiment, the agent is a cannabinoid, or derivative thereof including, for example, a cannabidiol or derivative thereof. In another embodiment, the cannabidiol or derivative thereof comprises the structure of Formula I comprising an alkyl side chain and an open pyrane ring wherein the cannabidiol derivative inhibits Id-1 expression, cancer cell proliferation, cancer cell invasion, metastasis or a combination thereof:

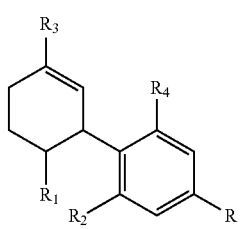

Formula I

In one aspect, $R^1$, $R^2$, $R^3$, $R^4$, are each independently selected from the group consisting of: H, —OH, aryl, substituted aryl, alkyl, substituted alkyl, carboxyl, aminocarbonyl, alkylsulfonylaminocarboxyl, and alkoxycarbonyl and wherein R is an alkyl, or substituted alkyl of at least 6 carbon atoms.

The disclosure also provides a method of treating cancer in a subject, comprising administering to a subject in need of such treatment a therapeutically effective amount of a composition comprising a combination of the cannabinoids cannabidiol (CBD) and tetrahydrocannabinol (THC).

The disclosure also provides a compound comprising the structure of Formula I having an alkyl side chain and an open pyrane ring, wherein R comprises at least 6 carbon atoms

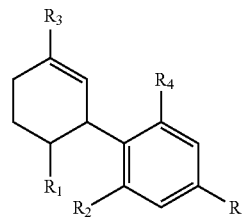

Formula I

In one embodiment, $R^1$, $R^2$, $R^3$, $R^4$, are each independently selected from the group consisting of: H, —OH, aryl, substituted aryl, alkyl, substituted alkyl, carboxyl, aminocarbonyl, alkylsulfonylaminocarboxyl, and alkoxycarbonyl and wherein R is an alkyl, or substituted alkyl of at least 6 carbon atoms.

In yet another aspect, the $R^1$, $R^2$, $R^3$, $R^4$, are each independently selected from the group consisting of: H, —OH, aryl, substituted aryl, alkyl, substituted alkyl, carboxyl, aminocarbonyl, alkylsulfonylaminocarboxyl, and alkoxycarbonyl and wherein R is an alkyl, or substituted alkyl of at least 6 carbon atoms. In one embodiment, the cancer is an epithelial cell cancer such as, for example, melanoma, breast carcinoma or lung carcinoma. In yet another embodiment, the cancer is brain cancer, such as glioblastoma multiforme. The method can further comprise administering a THC or derivative thereof. In another embodiment, the method can further include administering an effective amount of paclitaxel.

The disclosure also provides a method of treating cancer in a subject, comprising administering to a subject in need of such treatment a therapeutically effective amount of a composition comprising a cannabidiol or derivative thereof and a THC or a derivative thereof. In one embodiment, the cannabidiol or derivative thereof comprises the structure of Formula I comprising an alkyl side chain and an open pyrane ring wherein the cannabidiol derivative inhibits Id-1 expression

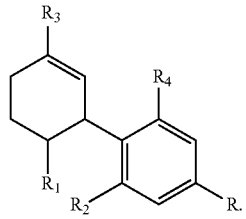

Formula I

The disclosure also provides a composition comprising a compound of formula I and a pharmaceutically acceptable carrier. The composition may further comprise a tetrahydrocannabinol (THC) or a derivative thereof.

The disclosure also provides a composition comprising a combination of the cannabinoids cannabidiol (CBD) and tetrahydrocannabinol (THC). In one embodiment, the composition further comprises a pharmaceutically acceptable carrier.

The disclosure demonstrates that the addition of CBD to $\Delta^9$-THC improves the overall potency and efficacy of $\Delta^9$-THC in the treatment of cancer (e.g., glioblasoma multiforme "GBM").

In some aspects, $\Delta^9$-THC in combination with a lower concentration of CBD, synergistically inhibits GBM cell growth and induces apoptosis. The inhibitory properties of the combination were the result of activation of $CB_2$ receptors and a corresponding increase in oxygen radical formation. The signal transduction mechanisms associated with the effects of the combination treatment were significantly different from those observed with the individual compounds.

Accordingly, provided herein are methods and compositions for treatment of cancer. Such compositions can comprise a combination of the cannabinoids cannabidiol (CBD) and tetrahydrocannabinol (THC).

One embodiment comprises a composition for treating cancer in a subject, the composition comprising a combination of the cannabinoids cannabidiol (CBD) and tetrahydrocannabinol (THC) or derivatives thereto.

In another embodiment, the composition can further include a compound suitable for treating a cell proliferation disorder, such as an anticancer drug (e.g. paclitaxel).

In another embodiment, the disclosure provides a method of treating cancer in a subject, comprising administering to a subject in need of such treatment a therapeutically effective amount of a composition comprising a combination of the cannabinoids cannabidiol (CBD) and tetrahydrocannabinol (THC).

The details of one or more embodiments of the disclosure are set forth in the accompanying drawings and the description below. Other features, objects, and advantages will be apparent from the description and drawings, and from the claims.

BRIEF DESCRIPTION OF DRAWINGS

The accompanying drawings, which are incorporated into and constitute a part of this specification, illustrate one or more embodiments of the invention and, together with the detailed description, serve to explain the principles and implementations of the invention.

FIG. 1A-E provide data indicating that CBD is an effective inhibitor of Id-1 and corresponding breast cancer proliferation and invasiveness in MDA-MD231 cells. (A) depicts the results of a Boyden chamber invasion assay used to determine the effects of cannabinoids on the invasiveness of aggressive human breast cancer MDA-MB231 cells. Compounds were added at concentrations of 0.1 µM, 1.0 µM, or 1.5 µM. Data are presented as relative invasiveness of the cells through the Matrigel, where the respective controls are set as 100%. (B) depicts Western blot analysis of proteins from MDA-MB231 cells treated with vehicle (control), 0.1 µM, 1.0 µM, or 1.5 µM of CBD for three days and analyzed as described below. (C) is a graph depicting the relative expression of Id-1 in treated cells/vehicle cells. Proteins from MDA-MB231 cells treated with additional cannabinoids for three days were extracted and analyzed for Id-1 by Western blot analysis. Normalization was carried out by stripping the blots and re-probing with a monoclonal anti-tubulin antibody. (D) is a graph depicting the inhibitory effect of 1.5 µM CBD on Id-1 expression compared over a time course of one-, two-, and three-days. (E) shows data depicting the structure activity relationship of cannabinoids and the regulation of Id-1 protein expression. Proteins from MDA-MB231 cells treated with vehicle (control) or 1.5 µM of various cannabinoid compounds for two days and then analyzed for Id-1 by Western blot analysis as described in the methods. A high molecular weight non-specific band was used as a loading control (LC). Data are the mean of at least three replicates; bars, ±SE. Data were compared using a one-way ANOVA with a corresponding Dunnett's post-hoc test. (*) indicates statistically significant differences from control ($p<0.05$).

FIG. 2A-C provides data indicating that CBD inhibits the expression of Id-1 gene at the mRNA and promoter levels in MDA-MB231 cells. (A) shows the inhibition of the Id-1 gene product (434 bp) by CBD. Expression of the ß-actin gene product (232 bp) was used as a control. (B) shows luciferase activity in MDA-MB231 cells transiently transfected with Id-1-sbsluc as determined in the presence of vehicle (control) or 1.5 µM CBD. Cells were treated for 2 days and luciferase activity was measured. (C) shows data for cells treated for 3 days. For both (B) and (C), all values were normalized for the amount of ß-gal activity present in the cell extracts. Data are the mean of at least three replicates; bars, ±SE. The data are represented as percentage of activity of the treated cells/vehicle cells×100. Data were compared using the unpaired Student's t-test. (*) indicates statistically significant differences from control ($p<0.05$).

FIG. 3A-F provides data indicating that combinations of $\Delta^9$-THC and CBD produce synergistic effects on the inhibition of cell growth in SF216 and U251 cells but not in U87 cells. A 2×2 factorial design was used. A) depicts results for SF126, B) for U251, C) for U87MG cells that were treated for three days with vehicle/no drug, $\Delta^9$-THC, CBD, or a combination of $\Delta^9$-THC and CBD. Concentrations of $\Delta^9$-THC and CBD that produce only minimal effects on cell proliferation (denoted low as opposed to high) were also tested in 2×2 factorial design in: D) for SF126, E) for U251 cells. Cell proliferation was measured using the MTT assay. The absorbance of the media alone at 570 nm was subtracted, and % control was calculated as the absorbance of the treated cells/control cells×100. F) is a representative light microscope image of the effects of the combination treatment on U251 cells from the experiment shown in (E) is presented (10×). Data are the mean of at least 3 independent experiments; bars, ±SE.

FIG. 4A-C shows combination treatment of $\Delta^9$-THC and CBD specifically inhibits ERK activity. The effects of cannabinoids on MAPK activity were analyzed using Western analysis. U251 cells were treated with vehicle or a combination of Δ9-THC (1.7 µM) and CBD (0.4 µM) for two days. Proteins were extracted and analyzed for A) pERK and total ERK, B) pJNK 1/2 and p38 MAPK. U251 cells were treated with Δ9-THC (1.7 µM) and CBD (0.4 µM) alone and analyzed for C) pERK and total ERK. Either α-tubulin or β-actin was used as a loading control (LC). Blots are representative of at least 3 independent experiments.

FIG. 5 shows data indicating that when combined, $\Delta^9$-THC and CBD produce greater than additive effects on the cell cycle inhibition and induction of apoptosis in U251 cells. U251 cells were treated for three days with Δ9-THC (1.7 µM), CBD (0.4 µM), or a 4:1 combination ratio [Δ9-

THC (1.7 μM)/CBD (0.4 μM)]. The number of cells staining positive for annexin (apoptosis) were measured using FACS analysis. % control was calculated as positive annexin staining of the treated cells minus control cells. Data are the mean of at least 3 independent experiments; bars, ±SE. Data were compared using a one-way ANOVA with a corresponding Tukey's post-hoc test. (*) indicates statistically significant differences from control (p<0.05).

FIG. 6A-E shows $CB_2$ activation and corresponding increases in oxygen radical formation are involved in the inhibitory effects of the cannabinoid combination treatment. The number of U251 cells staining positive for annexin (apoptosis) after 3 days treatment were measured using FACS analysis. Cells were treated with A) a 4:1 combination of $\Delta^9$-THC (1.7 μM) and CBD (0.4 μM) B) 2.5 μM $\Delta^9$-THC or C) 2.0 μM CBD in the presence of 0.5 μM of the $CB_1$ antagonist, SR141716A (SR1), 0.5 μM of the $CB_2$ antagonist, SR144528 (SR2) or 20 μM α-tocopherol (TCP). % control was calculated as positive annexin staining of the treated cells minus control cells. D) The effects of cannabinoids on pERK activity were analyzed using Western analysis. α-tubulin was used as a loading control (LC). U251 cells were treated with vehicle or the indicated drugs for three days. E) The production of cellular radical oxygen species (ROS)/$H_2O_2$ was measured using 2'7'Dichlorodihydrofluorescein and FACS analysis. U251 cells were treated with vehicle or a 4:1 combination of $\Delta^9$-THC (1.7 μM) and CBD (0.4 μM). Data are the mean of at least 3 independent experiments; bars, ±SE. Data were compared using a one-way ANOVA with a Bonferroni's multiple comparison post-hoc analyses. (*) indicates statistically significant differences from control (p<0.05). (#) indicates statistically significant differences from the combination treatment of THC/CBD (p<0.05).

FIG. 7A-C shows data indicating that ectopic expression of Id-1 blocks the effect of CBD on MDA-MB231 invasiveness. (A) provides representative light microscope images of control MDA-MB231 (−Id-1 cells, upper panels) and of MDA-MB231 cells that ectopically expressed Id-1 (+Id-1 cells, lower panels) after a two day treatment with vehicle (control) or 1.5 μM CBD, and then an overnight invasion assay. (B) provides data showing the relative invasiveness of the cells through the Matrigel, where the respective controls are set as 100%, and are the mean of at least three replicates; bars, ±SE. Data were compared using the unpaired Student's t-test. (*) indicates statistically significant differences from control (p<0.05). (C) is a Western blot showing the inhibitory effect of CBD on Id-1 expression in −Id-1 and +Id-1 MDA-MB231 cells was compared.

Figure 8:
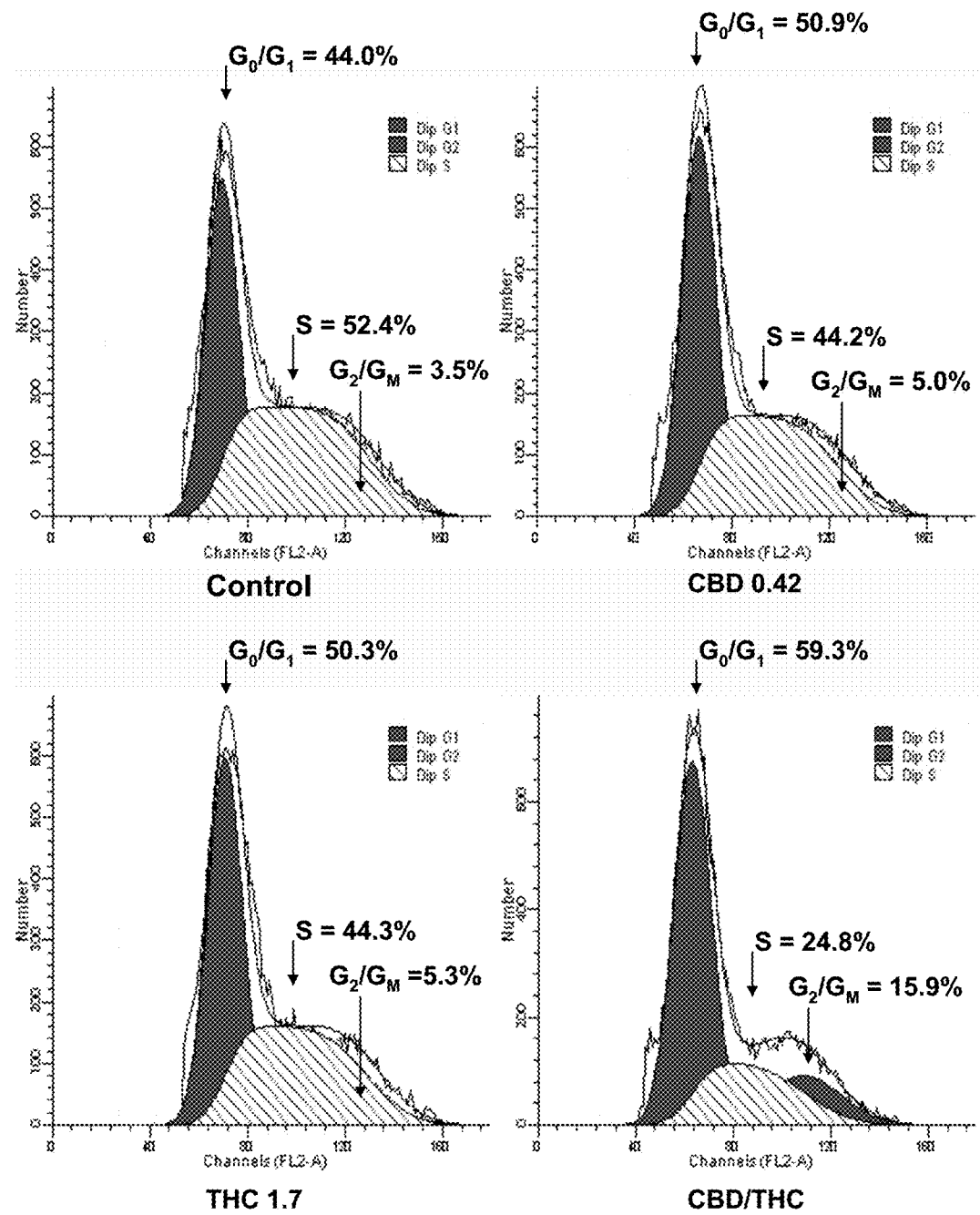

FIG. 8 shows that the combination treatment of $\Delta^9$-THC and CBD produces G1/S cell cycle arrest. Cell cycle was measured using PI staining and FACS analysis. U251 cells were treated for three days with Δ9-THC (1.7 μM), CBD (0.4 μM), or a combination of Δ9-THC (1.7 μM) and CBD (0.4 μM). Cells were collected and analyzed using a desktop FACS Calibur with Cell Quest Pro software. Modfit was used to determine the percentage of cell in $G_0/G_1$, S and $G_2/G_M$ phase.

Figure 9:
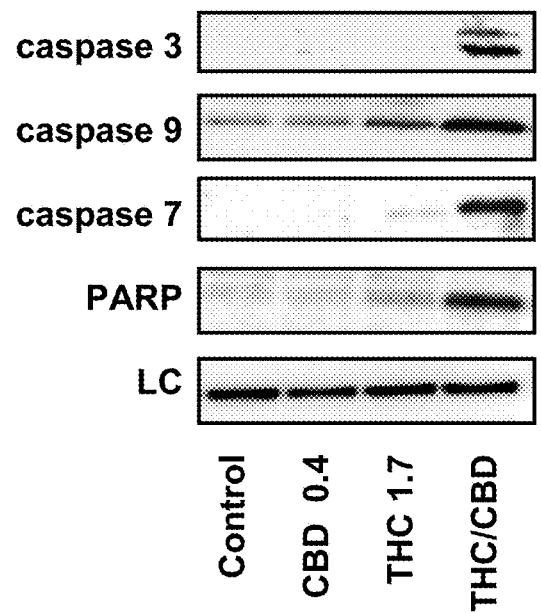

FIG. 9 shows that when combined, $\Delta^9$-THC and CBD produce a significant increase in activation of multiple caspases. The effects of cannabinoids on caspase and p8 expression were analyzed using Western analysis. U251 cells were treated for three days with Δ9-THC (1.7 μM), CBD (0.4 μM), or a combination of Δ9-THC (1.7 μM) and CBD (0.4 μM). Proteins were extracted and analyzed for cleaved caspase 3, 7, 9 and PARP. Blots are representative of at least 3 independent experiments.

Figure 10:
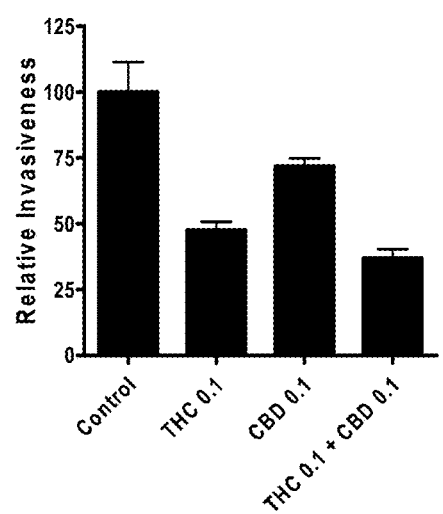

FIG. 10 is a graph showing that CBD was also able to significantly reduce the invasiveness of U251 cells.

Figure 11:
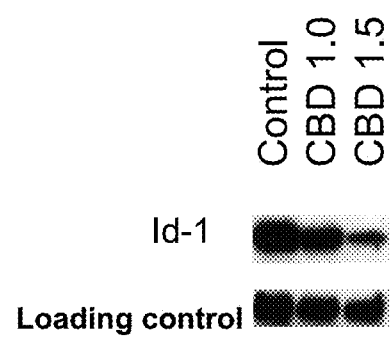

FIG. 11 is a blot showing that treatment of U251 cells with CBD led to a concentration-dependent inhibition of Id-1 protein expression.

DETAILED DESCRIPTION

As used herein and in the appended claims, the singular forms "a," "and," and "the" include plural referents unless the context clearly dictates otherwise. Thus, for example, reference to "a compound" includes a plurality of such compounds and reference to "the cancer" includes reference to one or more cancers, and so forth.

Also, the use of "or" means "and/or" unless stated otherwise. Similarly, "comprise," "comprises," "comprising," "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Any publications discussed above and throughout the text are provided solely for their disclosure prior to the filing date of the present application. Nothing herein is to be construed as an admission that the inventors are not entitled to antedate such disclosure by virtue of prior disclosure.

Activation of the two cannabinoid receptors, CB1 and CB2, can lead to the inhibition of cell proliferation and induction of apoptosis in multiple types of cancer cell lines resulting in the reduction of tumor growth in vivo (Guzman, 2003). The CB1 and CB2 receptors are members of the G-protein coupled receptor (GPCR) superfamily, and can interact with five structurally distinct classes of compounds. These include the plant-derived classical cannabinoids, such as Δ9-THC and CBN; the non-classical bicyclic cannabinoid agonists, such as CP55,940; the endogenous cannabinoid agonists, such as anandamide (AEA); and the aminoalkylindole (AAI) agonists, such as WIN55,212-2; and the antagonist/inverse agonists, such as SR141716A (Pertwee, 1997).

Interaction sites, independent of CB1 and CB2 receptors, may also be responsible for the anticancer activity of cannabinoids (Ruiz et al., 1999; McAllister et al., 2005). There are more than 60 cannabinoids in Cannabis sativa. In addition to Δ9-THC, the compounds cannabidiol (CBD), cannabinol (CBN), and cannabigerol (CBG) are also present in reasonable quantities (McPartland and Russo, 2001). CBN has low affinity for CB1 and CB2 receptors, whereas the non-psychotropic cannabinoids, CBD and CBG, have negligible affinity for the cloned receptors.

Previous studies demonstrated that the helix-loop-helix protein Id-1, an inhibitor of basic helix-loop-helix (bHLH) transcription factors, plays a crucial role during breast cancer progression. Id-1 stimulated proliferation, migration and invasion in breast cancer cells. Moreover, targeting Id-1 expression partially in breast cancer cells reduced invasion and breast cancer metastasis in vitro and in preclinical animal models. The disclosure shows that Id-1 is a target for therapy approaches, and that inhibiting Id-1 expression and/or activity provides a mechanism for treating patients with breast cancer. This approach may be highly effective and safe in advanced breast cancer patients, given (1) the relationship between high Id-1 expression levels and aggressive breast cancer cell behaviors; (2) partial reduction in Id-1 activity can achieve significant outcomes; and (3) Id-1 expression is low in normal adult tissues, thereby eliminating unwanted toxicities generally associated with currently available therapeutic modalities.

Id-1 protein plays a key role in the malignant progression of many aggressive and invasive human cancers such as: leukemia, melanoma, hepatocellular carcinoma, colorectal adenocarcinoma, pancreatic cancer, lung cancer, kidney cancer, medullary thyroid cancer, papillary thyroid cancer, astrocytic tumor, neuroblastoma, Ewing's sarcoma, ovarian tumor, cervical cancer, endometrial carcinoma, breast cancer, prostate cancer, malignant seminoma, and squamous cell carcinomas, such as esophageal cancer, and head and neck cancer. Accordingly, Id-1 associated cell proliferative disorders include, but are not limited to, Leukemia, Melanoma, Squamous cell carcinoma (SCC) (e.g., head and neck, esophageal, and oral cavity), Hepatocellular carcinoma, Colorectal adenocarcinoma, Pancreatic cancer, Lung cancer, Kidney cancer, Medullary thyroid cancer, Papillary thyroid cancer, Astrocytic tumor, Neuroblastoma, Ewing's sarcoma, Ovarian tumor, Cervical cancer, Endometrial carcinoma, Breast cancer, Prostate cancer, and Malignant seminoma.

Approaches for targeting Id-1 expression include gene therapy using antisense oligonucleotide, siRNA, non-viral or viral plasmid-based strategies. In addition, the development of new strategies to modulate Id-1 expression/functional activity include the identification of small molecules that modulate the activity of Id-1. A range of small molecules that target the molecular pathology of cancer are now being developed, and a significant number of them are being tested in ongoing human clinical trials. The disclosure demonstrates that cannabidiol (CBD) and CBD derivatives are inhibitors of Id-1. The use of CBD, and derivatives thereof, represents a novel strategy for the treatment of cancer.

As used herein, the term "CBD" and "CBD derivatives" includes cannabinoids and derivatives thereof such as cannabidiol. Cannabinoids are a group of terpenophenolic compounds present in *Cannabis sativa*. The term "cannabinoids" generally refers to a group of substances that are structurally related to tetrahydrocannabinol (THC) or that bind to cannabinoid receptors. Plant cannabinoids are stable compounds with low toxicity profiles that are well tolerated by animals and humans during chronic administration. A variety of chemical classes of cannabinoids are useful in the methods provided herein including cannabinoids structurally related to THC, aminoalkylindoles, the eicosanoids related to the endocannabinoids, 1,5-diarylpyrazoles, quinolines and arylsulphonamides and additional compounds that do not fall into these standard classes but bind to cannabinoid receptors. Exemplary structures are set forth below.

Data provided herein indicates that CBD and derivatives thereof that act as Id-1 inhibitor effectively inhibit genotypic and phenotypic changes that allow aggressive breast cancers to proliferate, invade and metastasize.

Since CBD inhibits Id-1 expression in aggressive breast cancer, the disclosure also provides a rational drug design strategy and compounds obtained there from as potent and efficacious analogs. The disclosure demonstrates that the opened tetrahydropyran ring in CBD and aliphatic side chain of CBD are key pharmacophores involved in the inhibition of Id-1, alterations of these functional groups allow one to improve both the potency and efficacy of the parent compound, CBD.

Moreover, reducing Id-1 expression with cannabinoids provides a therapeutic strategy for the treatment of additional aggressive cancers since Id-1 expression was found to be up-regulated during the progression of almost all types of solid tumors investigated.

Accordingly, provided herein are methods for modulating the activity of a metastatic cell by regulating the activity of a target Id-1 using a CBD or CBD derivative. Methods can also include "regulating the activity of a target Id-1" includes: 1) mechanisms for modulating endogenous nucleic acid sequences that encode a target Id-1 such that Id-1 polypeptide levels are decreased in a cell; 2) introducing exogenous nucleic acid sequences that inhibit Id-1 expression in a cell; 3) increasing the turnover rate of endogenous Id-1 polypeptides such that Id-1 polypeptide levels are decreased in a cell.

In some embodiments the methods described herein can be designed to identify substances that modulate the biological activity of a Id-1 by modulating the expression of an Id-1 nucleic acid sequence encoding an Id-1 polypeptide. For example, methods can be utilized to identify compounds that bind to Id-1 regulatory sequences. Alternatively, methods can be designed to identify substances that modulate the biological activity of a Id-1 by affecting the half-life of a Id-1 polypeptide.

In other embodiments, methods for treating a cell proliferation-related disorder are provided herein. Agents, substances or compounds that regulate the expression and/or activity of endogenous Id-1 or the half-life of endogenous Id-1 may be used for treating a cell proliferation-related disorder. In general these methods can be used in the treatment of conditions associated with disorders related to neoplastic cells and the metastasis thereof.

For administration to a subject, modulators of Id helix-loop-helix expression and/or activity (e.g., inhibitory agents, nucleic acid molecules, proteins, or compounds identified as modulators of a Id expression and/or activity) will preferably be incorporated into pharmaceutical compositions suitable for administration.

The disclosure also pertains to the field of predictive medicine in which diagnostic assays, prognostic assays, pharmacogenomics, and monitoring clinical trails are used for prognostic (predictive) purposes to thereby treat an individual prophylactically. As such, the disclosure contemplates use of methods provided herein to screen, diagnose, stage, prevent and/or treat disorders characterized by expression or over-expression of an Id helix-loop-helix polypeptide, such as Id-1. Accordingly, a subject can be screened to determine the level of a particular Id's expression or activity. A subject can also be screened for the susceptibility of neoplastic cells to techniques that inhibit the expression or over expression of an Id polypeptide.

The disclosure also provides for prognostic (or predictive) assays for determining whether an individual is at risk of developing a disorder associated with under expression of a target Id polypeptide. Such assays can be used for prognostic or predictive purpose to thereby prophylactically treat an individual prior to the onset of a disorder characterized by or associated with over expression or activity of a target Id polypeptide, such as Id-1.

The disclosure provides cannabinoid derivatives (e.g., cannabidiols). In one embodiment, the disclosure provides compositions comprising cannabinoids cannabidiol (CBD)

either alone or in combination with tetrahydrocannabinol (THC) or a derivative thereof. As described herein CBD and derivatives thereof are significantly more effective than other cannabinoid compounds at inhibiting the expression of genes and proteins that modulate cancer aggressiveness (e.g. Id-1) in, for example, breast cancer aggressiveness. The data also indicated that Id-1 is a key factor whose expression needed to be down-regulated in order for CBD to inhibit breast cancer cell aggressiveness. The down-regulation of gene expression produced by CBD was the result of the inhibition of the endogenous Id-1 promoter and its corresponding mRNA and protein levels. As shown in FIG. 1, CBD and derivatives thereof effectively inhibits the expression of Id-1 in MDA-MB231 metastatic breast cancer cells.

To determine general structural components of CBD that were responsible for its inhibitory activity, CBD was compared against structurally related cannabinoid compounds for their ability to inhibit Id-1 (FIG. 1). THC had no activity against Id-1. Δ9THC (THC) is structurally related to CBD with the primary exception being that the B ring or 1,1'-dimethyl-pyrane ring (FIG. 1E) of THC has been opened in CBD. CP55,940 (Formula IV, below) was a compound that inhibited Id-1 expression, however, it was still less effective than CBD. CP55,940 does have a open pyrane ring but the constituents within this area are significantly different compared to those present in CBD. Additionally, the alkyl chain is six carbons in length and contains a dimethyl heptyl addition. The data provided herein show that the unique activity (Id-1 inhibition) is related to the opened pyrane ring and the possession of an extended alkyl side chain.

The disclosure provides cannabidiol derivatives comprising an alkyl side chain and an open pyrane ring wherein the cannabidiol derivative inhibits Id-1. A general CBD derivative of the disclosure is set forth in Formula I, below:

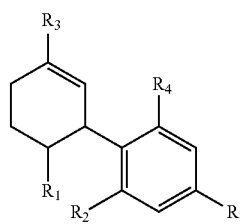

Formula I wherein R, $R^1$, $R^2$, $R^3$, $R^4$, are each independently selected from the group consisting of: H, aryl, substituted aryl, alkyl, substituted alkyl, carboxyl, aminocarbonyl, alkylsulfonylaminocarboxyl, and alkoxycarbonyl.

Alkyl groups include straight-chain, branched and cyclic alkyl groups. Alkyl groups include those having from 1 to 20 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms. Cyclic alkyl groups include those having one or more rings. Cyclic alkyl groups include those having a 3-, 4-, 5-, 6-, 7-, 8-, 9- or 10-member carbon ring. The carbon rings in cyclic alkyl groups can also carry alkyl groups. Cyclic alkyl groups can include bicyclic and tricyclic alkyl groups. Alkyl groups optionally include substituted alkyl groups. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cyclic alkenyl groups include those having one or more rings. Cyclic alkenyl groups include those in which a double bond is in the ring or in an alkenyl group attached to a ring. Cyclic alkenyl groups include those having a 3-, 4-, 5-, 6-, 7-, 8-, 9- or 10-member carbon ring. The carbon rings in cyclic alkenyl groups can also carry alkyl groups. Cyclic alkenyl groups can include bicyclic and tricyclic alkyl groups. Alkenyl groups are optionally substituted. Substituted alkenyl groups include among others those which are substituted with alkyl or aryl groups, which groups in turn can be optionally substituted.

Aryl groups include groups having one or more 5- or 6-member aromatic or heteroaromatic rings. Aryl groups can contain one or more fused aromatic rings. Heteroaromatic rings can include one or more N, O, or S atoms in the ring. Heteroaromatic rings can include those with one, two or three N, those with one or two O, and those with one or two S. Aryl groups are optionally substituted. Substituted aryl groups include among others those which are substituted with alkyl or alkenyl groups, which groups in turn can be optionally substituted.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups.

Alkylaryl groups are aryl groups substituted with one or more alkyl groups wherein the alkyl groups optionally carry additional substituents and the aryl groups are optionally substituted.

Optional substitution of any alkyl, alkenyl and aryl groups includes substitution with one or more of the following substituents: halogens, —CN, —COOR, —OR, —COR, —OCOOR, —CON(R)$_2$, —OCON(R)$_2$, —N(R)$_2$, —NO$_2$, —SR, —SO$_2$R, —SO$_2$N(R)$_2$ or —SOR groups. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for alkyl, alkenyl and aryl groups include among others:

—COOR where R is a hydrogen or an alkyl group or an aryl group and more specifically where R is methyl, ethyl, propyl, butyl, or phenyl groups all of which are optionally substituted;

—COR where R is a hydrogen, or an alkyl group or an aryl groups and more specifically where R is methyl, ethyl, propyl, butyl, or phenyl groups all of which groups are optionally substituted;

—CON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;

—OCON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;

—N(R)$_2$ where each R, independently of each other R, is a hydrogen, or an alkyl group, acyl group or an aryl group and more specifically where R is methyl, ethyl, propyl, butyl, or phenyl or acetyl groups all of which are optionally substituted; or R and R can form a ring which may contain one or more double bonds;

—SR, —SO$_2$R, or —SOR where R is an alkyl group or an aryl groups and more specifically where R is methyl, ethyl, propyl, butyl, phenyl groups all of which are optionally substituted; for —SR, R can be hydrogen;

—OCOOR where R is an alkyl group or an aryl groups;

—SO$_2$N(R)$_2$ where R is a hydrogen, an alkyl group, or an aryl group and R and R can form a ring;

—OR where R=H, alkyl, aryl, or acyl; for example, R can be an acyl yielding —OCOR* where R* is a hydrogen or an alkyl group or an aryl group and more specifically where R* is methyl, ethyl, propyl, butyl, or phenyl groups all of which groups are optionally substituted.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

Pharmaceutically acceptable salts of CBD and CBD derivatives of the disclosure are also included. For example, a pharmaceutically acceptable salt can comprise pharmaceutically-acceptable anions and/or cations. Pharmaceutically-acceptable cations include among others, alkali metal cations (e.g., Li$^+$, Na$^+$, K$^+$), alkaline earth metal cations (e.g., Ca$^{2+}$, Mg$^{2+}$), non-toxic heavy metal cations and ammonium (NH$_4^+$) and substituted ammonium (N(R')$_4^+$, where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include among other halides (e.g., Cl$^-$, Br$^-$), sulfate, acetates (e.g., acetate, trifluoroacetate), ascorbates, aspartates, benzoates, citrates, and lactate.

Compounds of the disclosure can have prodrug forms. Prodrugs of the compounds are useful in the methods of this disclosure. Any compound that will be converted in vivo to provide a biologically, pharmaceutically or therapeutically active form of a compound of the disclosure is a prodrug. Various examples and forms of prodrugs are well known in the art. Examples of prodrugs are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392).

In one embodiment, the CBD or CBD derivative comprises Formula I, wherein R is an alkyl comprising from 2-10 carbon atoms. Typically the alkyl will comprise at least 6 carbon atoms (e.g., 6, 7, 8, 9 or more carbon atoms). In some embodiments, the compound comprises an R$_1$, R$_2$, R$_3$, or R$_4$ that is the same as CBD (e.g., R$_1$ comprises a branched alkene, R$_3$ comprises a methyl group, R$_2$ and R$_4$ are hydroxyl groups). Alternatively, R$_1$ can be a branched chain alkyl and R$_2$ can be a methyl group. In yet another embodiment, the compound of Formula I comprises an R group selected from a group consisting of:

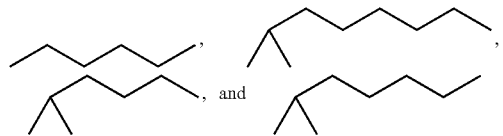

In yet another embodiment, R is selected from a member of the group above and R$_3$ is an ethyl group.

In another embodiment, the disclosure provides a compound of Formula I wherein R comprises a dimethylheptyl (DMH) analog or derivative thereof. In yet a further embodiment, the disclosure provides a compound of Formula I, wherein R comprises a DMH analog or derivative thereof and R$_3$ comprises an ethyl group.

Exemplary CBD compounds and CBD derivative compounds are set forth below and it will be recognized that such compounds can include prodrugs, salts and ethers thereof.

| Type | Skeleton | Cyclization |
|---|---|---|
| Cannabigerol-type CBG | | |
| Cannabichromene-type CBC | | |
| Cannabidiol-type CBD | | |
| Tetrahydrocannabinol- and Cannabinol-type THC, CBN | | |
| Cannabielsoin-type CBE | | |
| iso-Tetrahydrocannabinol-type iso-THC | | |
| Cannabicyclol-type CBL | | |

-continued
| Type | Skeleton | Cyclization |
|---|---|---|
| Cannabicitran-type CBT | 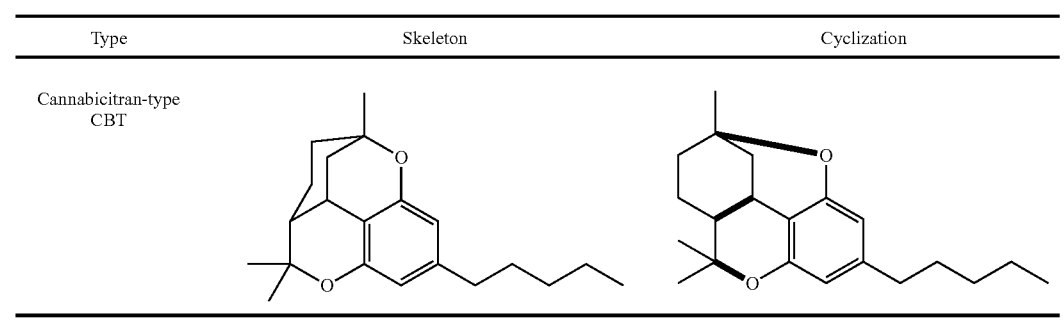 | |
-continued
(II)
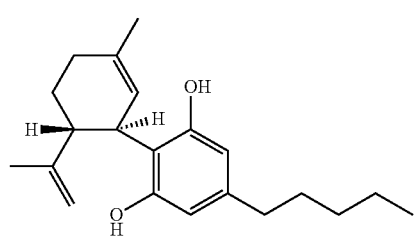
(III)
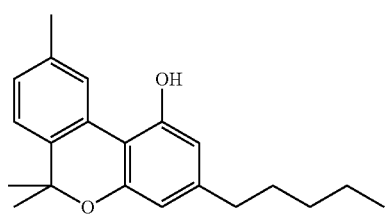
(IV)
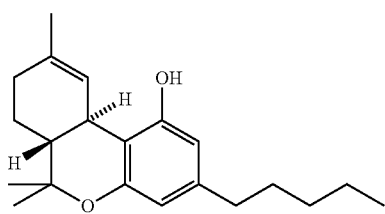
(V)
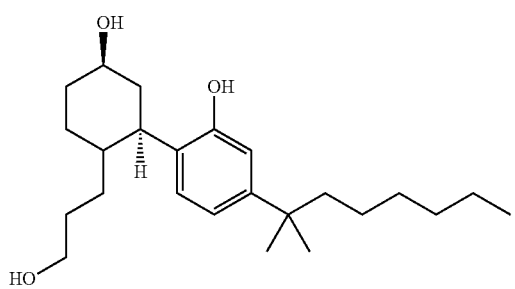
(VI)
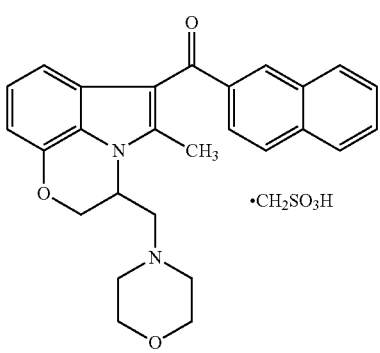
•CH$_2$SO$_3$H
| Cannabigerol-type (CBG) |
|---|
| 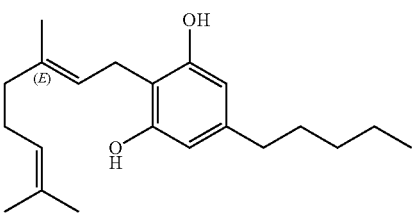 Cannabigerol (E)-CBG-C$_5$ |
| 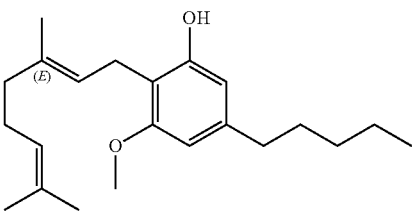 [SMILES: CCCCCc1cc(O)c(C/C=C(\C)CCC=C(C)C)c(O)c1] Cannabigerol monomethyl ether (E)-CBGM-C$_5$ A |

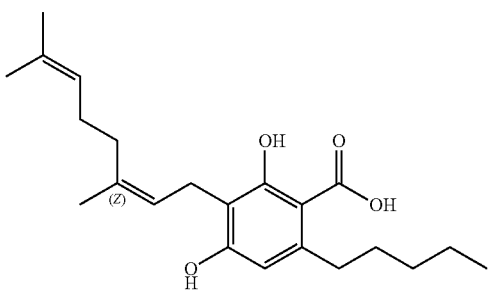

Cannabinerolic acid A
(Z)-CBGA-C$_5$ A

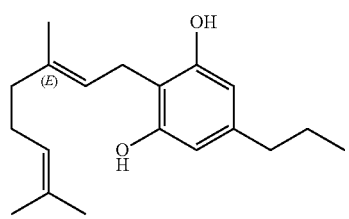

Cannabigerovarin
(E)-CBGV-C$_3$

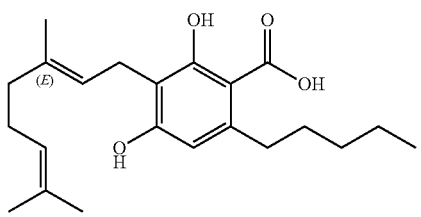

Cannabigerolic acid A
(E)-CBGA-C$_5$ A

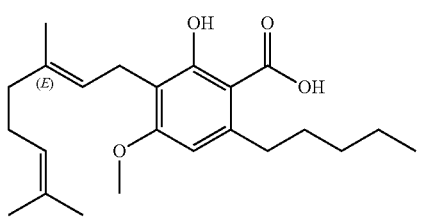

Cannabigerolic acid A
monomethyl ether
(E)-CBGAM-C$_5$ A

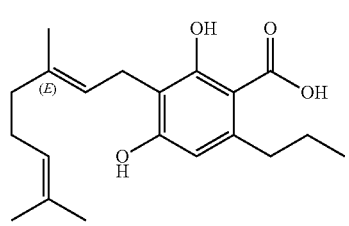

Cannabigerovarinic acid A
(E)-CBGVA-C$_3$ A

Cannabichromene-type (CBC)

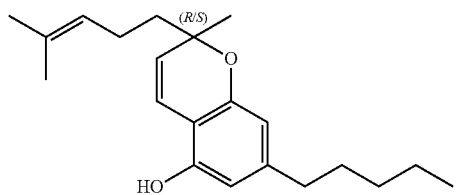

(±)-Cannabichromene
CBC-C$_5$

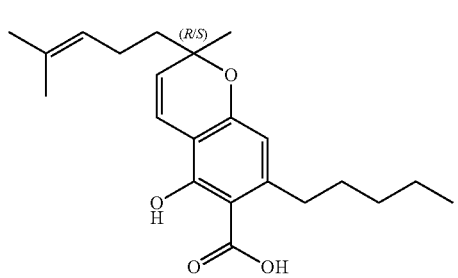

(±)-Cannabichromenic acid A
CBCA-C$_5$ A

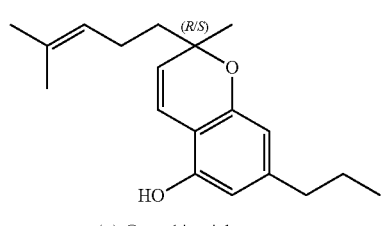

(±)-Cannabivarichromene,
(±)-Cannabichromevarin
CBCV-C$_3$

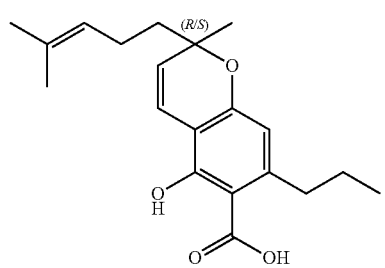

(±)-Cannabichromevarinic acid A
CBCVA-C$_3$ A

Cannabidiol-type (CBD)

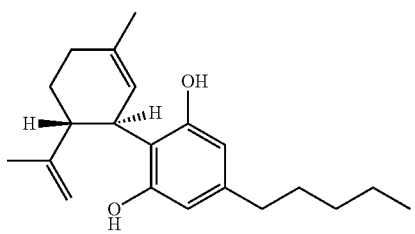

(−)-Cannabidiol
CBD-$C_5$

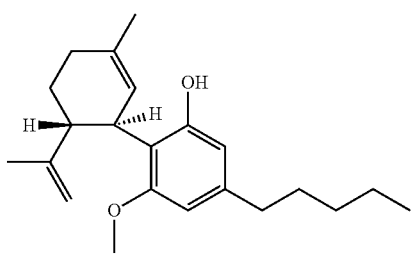

Cannabidiol
monomethyl ether
CBDM-$C_5$

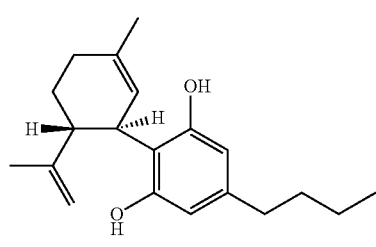

Cannabidiol-$C_4$
CBD-$C_4$

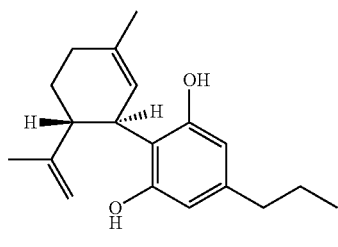

(−)-Cannabidivarin
CBDV-$C_3$

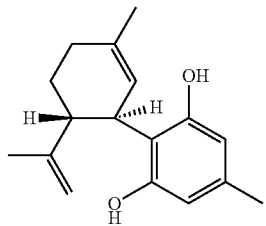

Cannabidiorcol
CBD-$C_1$

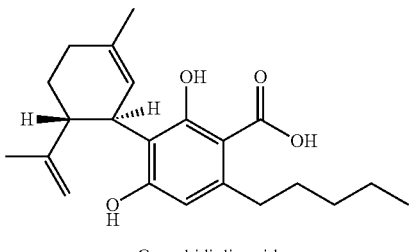

Cannabidiolic acid
CBDA-$C_5$

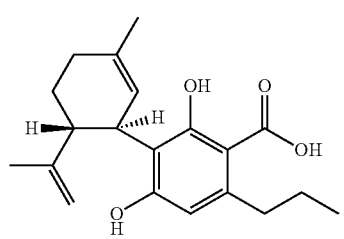

Cannabidivarinic acid
CBDVA-$C_3$

Cannabinodiol-type (CBND)

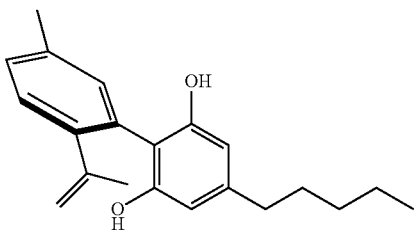

Cannabinodiol
CBND-$C_5$

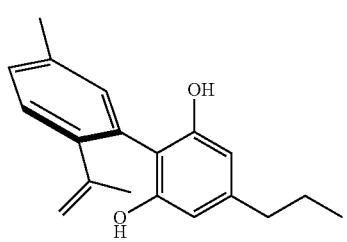

Cannabinodivarin
CBND-$C_3$

Tetrahydrocannabinol-type (THC)

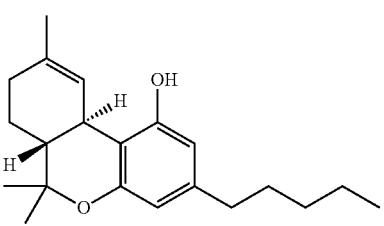

$\Delta^9$-Tetrahydrocannabinol
$\Delta^9$-THC-$C_5$

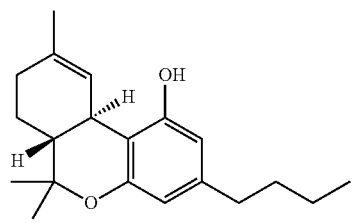

Δ⁹-Tetrahydrocannabinol-C₄
Δ⁹-THC-C₄

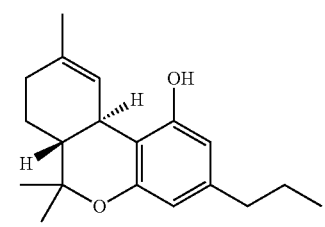

Δ⁹-Tetrahydrocannabivarin
Δ⁹-THCV-C₃

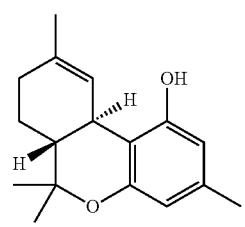

Δ⁹-Tetrahydrocannabiorcol
Δ⁹-THCO-C₁

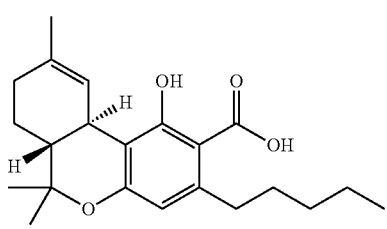

Δ⁹-Tetrahydrocannabinolic acid A
Δ⁹-THCA-C₅ A

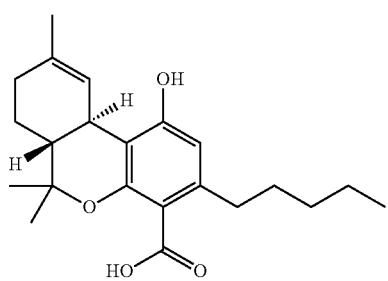

Δ⁹-Tetrahydrocannabinolic acid B
Δ⁹-THCA-C₅ B

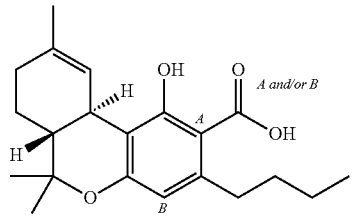

Δ⁹-Tetrahydrocannabinolic acid-C₄
A and/or B
Δ⁹-THCA-C₄ A and/or B

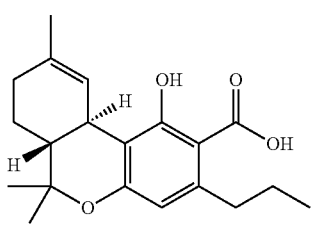

Δ⁹-Tetrahydrocannabivarinic acid A
Δ⁹-THCVA-C₃ A

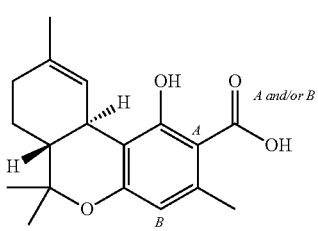

Δ⁹-Tetrahydrocannabiorcolic acid
A and/or B
Δ⁹-THCOA-C₁ An and/or B

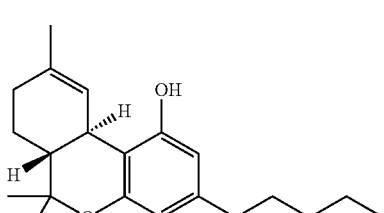

(−)-Δ⁸-trans-(6aR,10aR)-
Δ⁸-Tetrahydrocannabinol
Δ⁸-THC-C₅

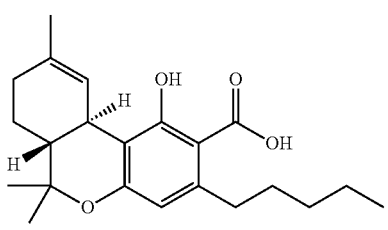

(−)-Δ⁸-trans-(6aR,10aR)-
Tetrahydrocannabinolic acid A
Δ⁸-THCA-C₅ A

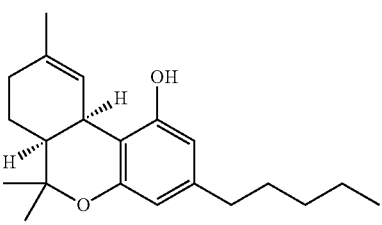
(−)-(6aS,10aR)-Δ⁹-
Tetrahydrocannabinol
(−)-cis-Δ⁹-THC-C₅
Cannabinol-type (CBN)
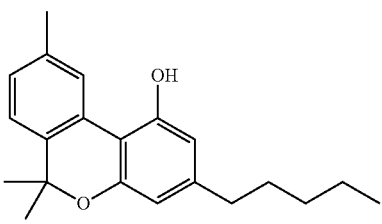
Cannabinol
CBN-C₅
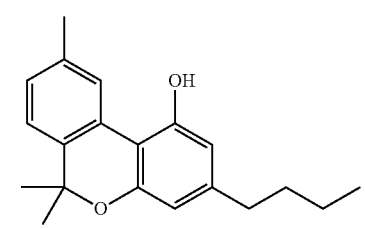
Cannabinol-C₄
CBN-C₄
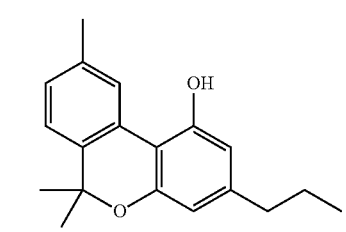
Cannabivarin
CBN-C₃
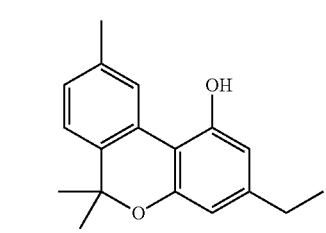
Cannabinol-C₂
CBN-C₂
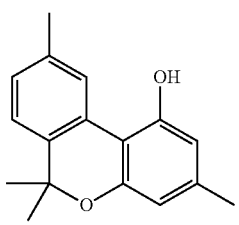
Cannabiorcol
CBN-C₁
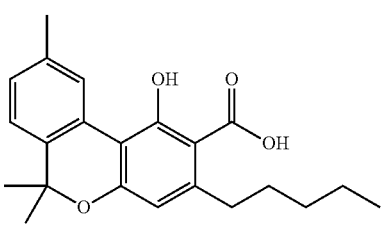
Cannabinolic acid A
CBNA-C₅ A
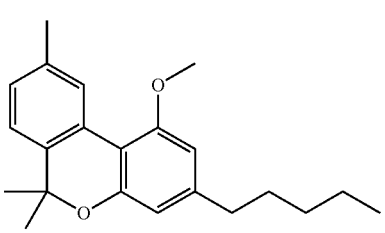
Cannabinol methyl ether
CBNM-C₅
Cannabitriol-type (CBT)
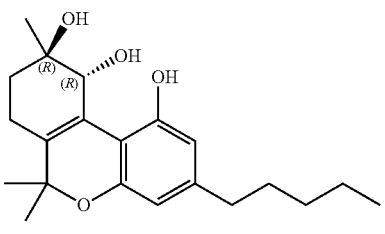
(−)-(9R,10R)-trans-
Cannabitriol
(−)-trans-CBT-C₅
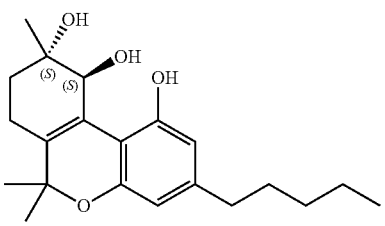
(+)-(9S,10S)-Cannabitriol
(+)-trans-CBT-C₅

-continued

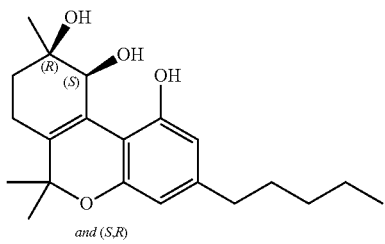

(±)-(9R,10S/9S,10R)-Cannabitriol
(±)-cis-CBT-C$_5$

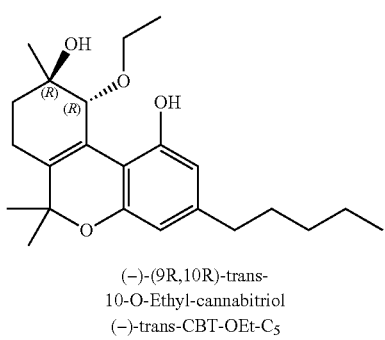

(−)-(9R,10R)-trans-
10-O-Ethyl-cannabitriol
(−)-trans-CBT-OEt-C$_5$

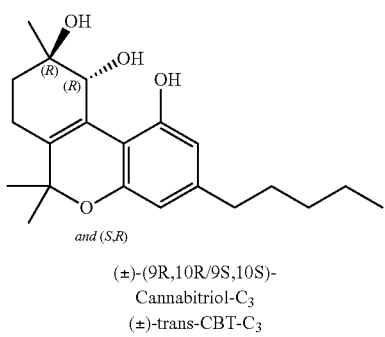

(±)-(9R,10R/9S,10S)-
Cannabitriol-C$_3$
(±)-trans-CBT-C$_3$

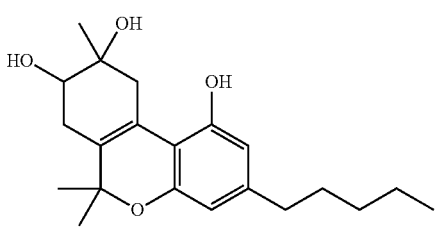

8,9-Dihydroxy-Δ$^{6a(10a)}$-
tetrahydrocannabinol
8,9-Di-OH-CBT-C$_5$

-continued

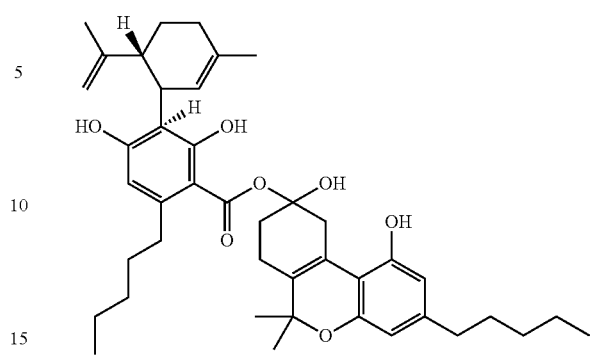

Cannabidiolic acid A
cannabitriol ester
CBDA-C$_5$ 9-OH-CBT-C$_5$ ester

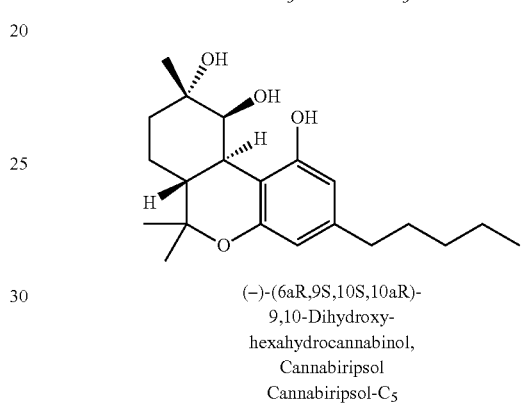

(−)-(6aR,9S,10S,10aR)-
9,10-Dihydroxy-
hexahydrocannabinol,
Cannabiripsol
Cannabiripsol-C$_5$

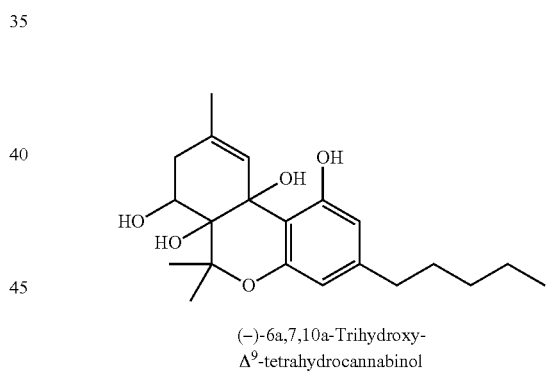

(−)-6a,7,10a-Trihydroxy-
Δ$^9$-tetrahydrocannabinol
(−)-Cannabitetrol

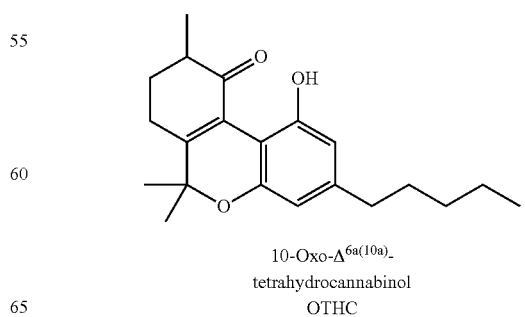

10-Oxo-Δ$^{6a(10a)}$-
tetrahydrocannabinol
OTHC

Cannabielsoin-type (CBE)

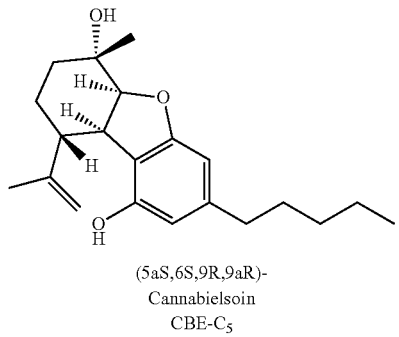

(5aS,6S,9R,9aR)-
Cannabielsoin
CBE-$C_5$

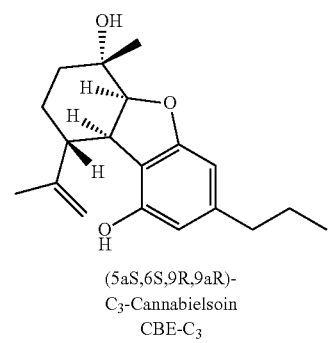

(5aS,6S,9R,9aR)-
$C_3$-Cannabielsoin
CBE-$C_3$

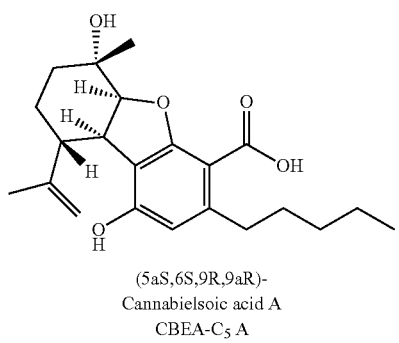

(5aS,6S,9R,9aR)-
Cannabielsoic acid A
CBEA-$C_5$ A

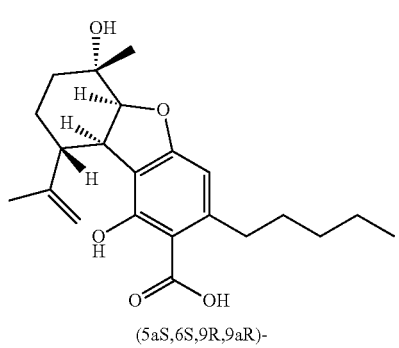

(5aS,6S,9R,9aR)-
Cannabielsoic acid B
CBEA-$C_5$ B

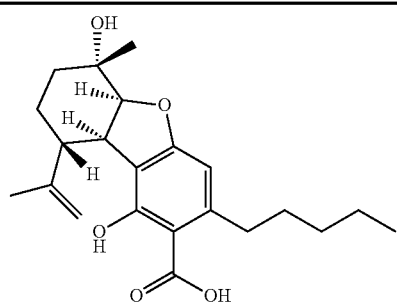

(5aS,6S,9R,9aR)-
$C_3$-Cannabielsoic acid B
CBEA-$C_3$ B

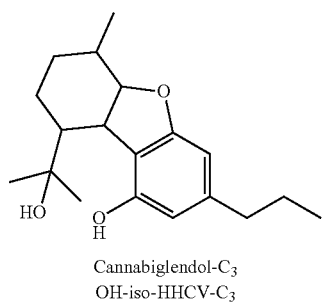 [SMILES: CCCc1cc(O)c2c(c1)OC1C(C)CCC(C(C)(C)O)C21]

Cannabiglendol-$C_3$
OH-iso-HHCV-$C_3$

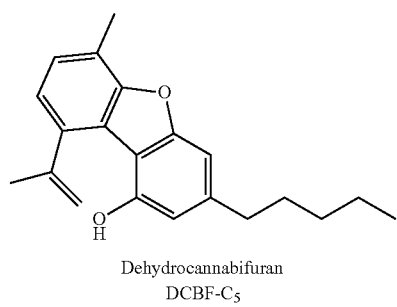 [SMILES: C=C(C)c1ccc(C)c2oc3cc(CCCCC)cc(O)c3c12]

Dehydrocannabifuran
DCBF-$C_5$

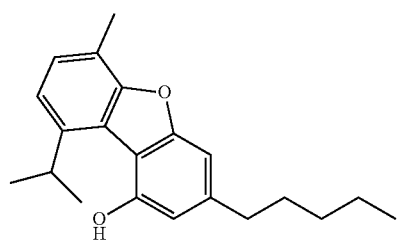

Cannabifuran
CBF-$C_5$

Isocannabinoids

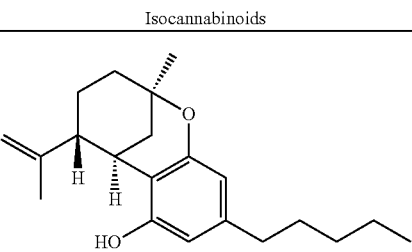

(−)-$\Delta^7$-trans-(1R,3R,6R)-
Isotetrahydrocannabinol

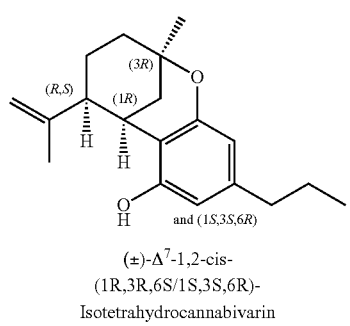 [SMILES: C=C(C)[C@H]1CC[C@]2(C)C[C@H]1c1c(O)cc(CCC)cc1O2]

(±)-Δ⁷-1,2-cis-
(1R,3R,6S/1S,3S,6R)-
Isotetrahydrocannabivarin

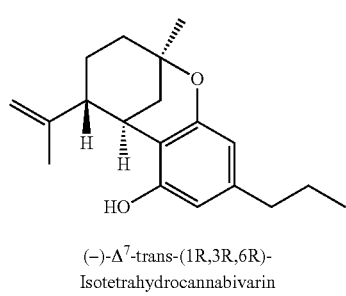 [SMILES: C=C(C)[C@@H]1CC[C@]2(C)C[C@H]1c1c(O)cc(CCC)cc1O2]

(−)-Δ⁷-trans-(1R,3R,6R)-
Isotetrahydrocannabivarin

Cannabicyclol-type (CBL)

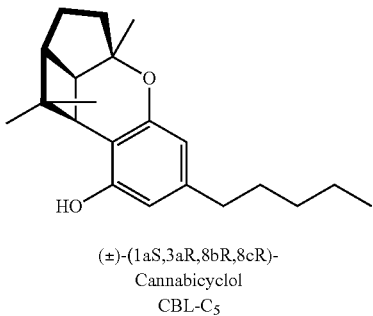

(±)-(1aS,3aR,8bR,8cR)-
Cannabicyclol
CBL-C₅

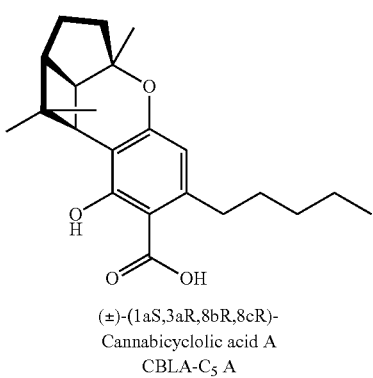

(±)-(1aS,3aR,8bR,8cR)-
Cannabicyclolic acid A
CBLA-C₅ A

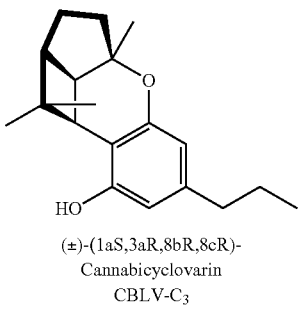

(±)-(1aS,3aR,8bR,8cR)-
Cannabicyclovarin
CBLV-C₃

Cannabicitran-type (CBT)

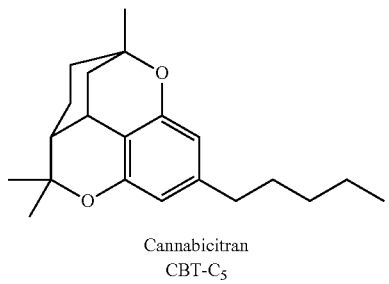 [SMILES: CCCCCc1cc2c3c(c1)OC(C)(C)C1CCC(C)(CC31)O2]

Cannabicitran
CBT-C₅

Cannabichromanone-type (CBCN)

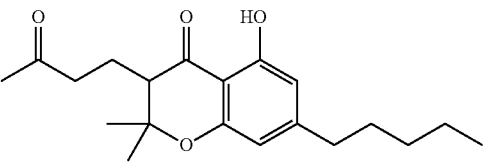

Cannabichromanone
CBCN-C₅

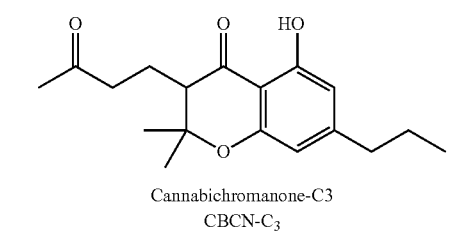 [SMILES: CCCc1cc(O)c2c(c1)OC(C)(C)C(CCC(C)=O)C2=O]

Cannabichromanone-C3
CBCN-C₃

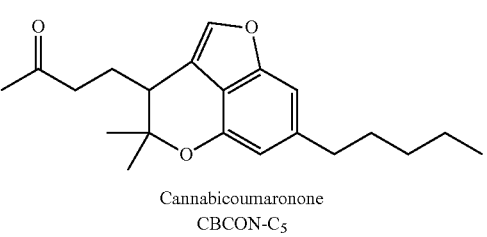 [SMILES: CCCCCc1cc2c3c(coc3c1)C(CCC(C)=O)C(C)(C)O2]

Cannabicoumaronone
CBCON-C₅

Miscellaneous

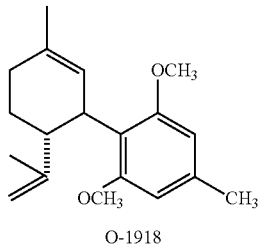 [SMILES: C=C(C)[C@@H]1CCC(C)=CC1c1c(OC)cc(C)cc1OC]

O-1918

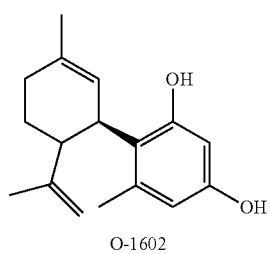 [SMILES: C=C(C)C1CCC(C)=C[C@H]1c1c(C)cc(O)cc1O]

O-1602

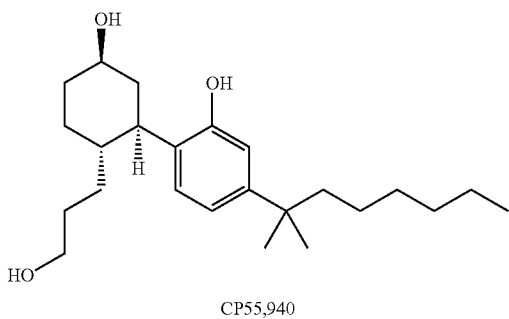 [SMILES: CCCCCCC(C)(C)c1ccc([C@@H]2C[C@H](O)CC[C@H]2CCCO)c(O)c1]

CP55,940

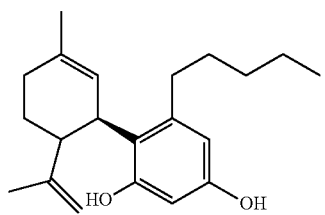

Abn-CBD

The disclosure demonstrates the antiproliferative activities of three groups of cannabinoid compounds. The groups included: 1) natural *cannabis* constituents that have affinity for $CB_1$ and $CB_2$ receptors, $\Delta^9$-THC and CBN; 2) synthetic cannabinoid analogs that have high affinity for $CB_1$ and $CB_2$ receptors, WIN 55,212-2 and CP55,940; and 3) natural *cannabis* constituents that do not have appreciable affinity for $CB_1$ and $CB_2$ receptors, CBD and CBG. Breast cancer cells were treated for three days and $IC_{50}$ values were calculated and provided in Table 1 below:

| Compound | MDA-MB231 | MDA-MB436 |
| --- | --- | --- |
| $\Delta^9$-THC | 1.2 (1.0-1.4) | 2.5 (1.8-3.4) |
| CBN | 1.2 (0.9-1.5) | 2.6 (1.8-3.7) |
| WIN 55, 212-2 | 1.7 (1.5-2.2) | 2.4 (1.6-3.4) |
| CP 55, 940 | 2.5 (1.5-4.1) | 1.3 (0.7-1.6) |
| CBD | 1.3 (1.0-1.9) | 1.5 (1.0-1.9) |
| CBG | 2.3 (2.1-2.5) | 2.1 (1.5-3.0) |

The rank order of potencies for the anti-proliferative effects of the cannabinoids in MDA-MB231 cells was: CBD=$\Delta^9$-THC=CBN>WIN55,212-2>CBG=CP55,940. The rank order of potencies for the antiproliferative effects of the cannabinoids in MDA-MB436 cells was: CBD=CP55,940>CBG=WIN55,212-2=$\Delta$9-THC=CBN. The data demonstrates that cannabidiol (CBD) is an effective inhibitor of human breast cancer cell aggressiveness, invasiveness, and therefore metastasis.

Invasion is an important step towards breast cancer cell metastasis. Therefore, the effects of several cannabinoids were tested on their ability to modulate the migratory and invasiveness activity of the most aggressive human breast cancer cell line, MDA-MB231, in a reconstituted basement membrane in a Boyden chamber. All three compounds tested, i.e., CBD, $\Delta^9$-THC, and WIN 55,212-2, significantly reduced the invasion of MDA-MB231 cells (FIG. 1, panel A). Again, as was observed with the cell aggressiveness and invasiveness experiments, the most potent inhibitor of invasion was CBD. The $IC_{50}$ value and corresponding confidence limits for CBD were 260 nM (110-610).

The compounds described herein and compositions comprising the compounds are useful to modulate the expression and/or activity of Id-1 in proliferating cells. In one exemplary embodiment, the information provided herein demonstrates a role for cannabidiols, and derivatives thereof, in inhibiting the metastasis through inhibition of Id-1 expression and/or activity.

Accordingly, the compositions and CBD compounds can be used in methods for modulating metastatic cancer cell progression by regulating the expression and/or activity of Id-1. The methods include using a pharmaceutical composition that includes an agent that modulates the expression and/or activity of Id-1. Exemplary agents include cannabinoid derivatives, such as cannabidiol and derivatives thereof.

U.S. patent application Ser. No. 11/390,682, and International application No. PCT/US01/2881, are hereby incorporated by reference, in their entirety for all purposes. While these publications provide general information about Id-1, it is understood that they do not propose or describe the methods provided herein.

The cannabidiols and derivatives can be used alone or in combination with other cannabidiols or derivatives or with THC or derivatives thereof. Compositions and formulations of the cannabidiols, derivatives and combinations thereof or in combination with THC can be used to treat cancer and other cell proliferative disorders.

Non-psychoactive cannabinoids, compounds that do not interact efficiently with cannabinoid 1 ($CB_1$) and ($CB_2$) receptors, can modulate the actions of $\Delta^9$-THC. The experiments described below, using multiple human (GBM) cells lines, compared the antiproliferative activity of non-psychoactive cannabinoids to synthetic and natural $CB_1$ and $CB_2$ agonists. The activity of $\Delta^9$-THC was tested in combination with CBD. In U251 and SF126 cell lines, $\Delta^9$-THC in combination with a lower concentration of CBD, acted synergistically to inhibit GBM cell growth and induce apoptosis. The inhibitory properties of the combination were the result of activation of $CB_2$ receptors and a corresponding increase in oxygen radical formation. The signal transduction mechanisms associated with the effects of the combination treatment were different from those observed with the individual compounds. The disclosure demonstrates that the addition of CBD to $\Delta^9$-THC improves the overall potency and efficacy of $\Delta^9$-THC in the treatment of patients with cell proliferative disorders such as, for example, GBM.

It was determined that $\Delta^9$-THC and CBD act synergistically to inhibit the growth of multiple GBM cell lines. It has been suggested that non-psychoactive cannabinoid constituents can either potentiate or inhibit the actions of $\Delta^9$-THC (Krantz et al., 1971; Jones and Pertwee, 1972; Poddar et al., 1974; McPartland and Russo, 2001). The $CB_1$ and $CB_2$ receptor agonist, $\Delta^9$-THC, can inhibit GBM growth in vitro and in vivo. CBD, a cannabinoid constituent with negligible affinity for $CB_1$ and $CB_2$ receptors can also inhibit the growth of GBM in vitro and in vivo. The disclosure demonstrates that of the non-psychoactive cannabinoids, CBD was the most potent inhibitor of GBM cell growth. Therefore, next the positive and negative aspects of constituent interaction was determined by testing multiple different concentration combinations of $\Delta^9$-THC and CBD in a 2×2 design. The three GBM cell lines that were originally used to screen the antiproliferative activity of individual cannabinoid (Table 1) were next used to determine the effects of combination treatments. When applied in combination, $\Delta^9$-THC and CBD produces synergistic inhibition of cell growth in SF126 and U251 cells but not in U87 cells (FIG. 3, Panels A, B, C). Concentrations of $\Delta^9$-THC and CBD alone that produce only minimal effects on cell proliferation were combined and further tested in a 2×2 factorial design in the positive responding cell lines (SF126 and U251) (FIG. 3, Panels D, E, F). The most pronounced synergistic activity was observed with U251 cells, therefore, this cell lines was used to determine the mechanism of action for the combination effect. The 4:1 (1.7 µM: 0.4 µM) ratio of $\Delta^9$-THC and CBD was used for the remainder of the experiments.

The disclosure demonstrates that the combination treatment of $\Delta^9$-THC and CBD leads to the modulation of specific mitogen activated kinases (MAPK). The regulation of ERK, JNK, and p38 MAPK activity plays a critical role in controlling cell growth and apoptosis (Chang et al., 2003). Therefore in U251 cells, it was determined whether treatment with a combination of $\Delta^9$-THC and CBD could alter the activity of ERK, JNK, and p38 MAPK. Treatment with the combination of cannabinoids led to a profound down-regulation of p-ERK but no significant change in total ERK (FIG. 4). Additionally, no inhibition of JNK or p38 MAPK activity was observed (FIG. 4). When U251 cells were treated with individual concentration of $\Delta^9$-THC and CBD, instead of the combination, no changes in pERK were observed.

The disclosure further demonstrates that the combination treatment of $\Delta^9$-THC and CBD induces apoptosis. Significant reductions in ERK activity have been shown to lead to induction of apoptosis (Chang et al., 2003). The large reduction in GBM cell growth and ERK activity, observed in the presence of the combination treatment of $\Delta^9$-THC and CBD, led to the prediction that there would be a corresponding modulation of programmed cell death. The measure of apoptosis (annexin staining) was used to probe additional mechanism involved in the synergistic activity of the THC/CBD combination. When $\Delta^9$-THC and CBD were combined a large increase in apoptosis was observed (FIG. 5). Separately 1.7 µM $\Delta^9$-THC and 0.4 µM CBD did not produce significant changes in apoptosis.

The disclosure demonstrates that the synergistic inhibitory effects of combination treatment are the result of $CB_2$ receptor activation and production of oxygen radicals. Depending on the cancer cell line and compound used, studies have linked the inhibitory activity of cannabinoids to activation of $CB_1$, $CB_2$, vanilloid (VR1) receptors, and the production of oxygen radicals (Maccarrone et al., 2000; Jacobsson et al., 2001; Bifulco and Di Marzo, 2002; Guzman, 2003; Massi et al., 2006; McKallip et al., 2006).

Apoptosis produced by the combination of $\Delta^9$-THC and CBD was partially blocked by the $CB_2$ receptor antagonist, SR144528, and fully reversed in the presences of α-tocopherol (oxygen radical scavenger) (FIG. 4). The vanilloid receptor antagonist, capsazepine did not block any of the effects observed with the combination treatment.

Accordingly, provided herein are compositions for treating cancer. Such compositions can comprise a combination of the cannabinoids cannabidiol (CBD) and tetrahydrocannabinol (THC).

In another embodiment, the composition can further include a compound suitable for treating a cell proliferation disorder, such as paclitaxel.

In another embodiment, a method of treating cancer in a subject, comprises administering to a subject in need of such treatment a therapeutically effective amount of a composition consisting essentially of a combination of the cannabinoids cannabidiol (CBD) and tetrahydrocannabinol (THC).

For administration to a subject, compositions are typically incorporated into pharmaceutical compositions suitable for administration.

Such compositions typically comprise compounds and a pharmaceutically acceptable carrier. Pharmaceutically acceptable carriers include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the disclosure is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In one embodiment, compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations should be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

The disclosure provides a method of using cannabinoids, or derivatives thereof (e.g., cannabidiols), as described herein, to treat cell proliferative disorders and metastasis. The cannabinoids and cannabidiol derivatives can be administered alone or in a pharmaceutically acceptable carrier. In other embodiments, the cannabinoids or cannabidiol derivatives can be administered in combination with a second biological active agent. In one embodiment, the second biological active agent is a THC compound or derivative. In yet another embodiment, the second biological active agent is an anticancer drug. Suitable anticancer drugs can be selected from the group consisting of methotrexate (Abitrexate®), fluorouracil (Adrucil®), hydroxyurea (Hydrea®), mercaptopurine (Purinethol®), cisplatin (Platinol®), daunorubicin (Cerubidine®), doxorubicin (Adriamycin®), etoposide (VePesid®), Vinblastine (Velban®), Vincristine (Oncovin®) and Pacitaxel (Taxol®).

A "cell proliferative disorder" is any cellular disorder in which the cells proliferate more rapidly than normal tissue growth. Thus a "proliferating cell" is a cell that is proliferating more rapidly than normal cells. The proliferative disorder, includes but is not limited to neoplasms. A "neoplasm" is an abnormal tissue growth, generally forming a distinct mass that grows by cellular proliferation more rapidly than normal tissue growth. Neoplasms show partial or total lack of structural organization and functional coordination with normal tissue. These can be broadly classified into three major types. Malignant neoplasms arising from epithelial structures are called carcinomas, malignant neoplasms that originate from connective tissues such as muscle, cartilage, fat or bone are called sarcomas and malignant tumors affecting hematopoetic structures (structures pertaining to the formation of blood cells) including components of the immune system, are called leukemias and lymphomas. A tumor is the neoplastic growth of the disease cancer. As used herein, a neoplasm, also referred to as a "tumor", is intended to encompass hematopoietic neoplasms as well as solid neoplasms. Other proliferative disorders include, but are not limited to neurofibromatosis, melanoma, breast cancers, head and neck cancers (e.g., brain cancers such as glioblastoma multiforme), gastrointestinal cancers and the like. A cancer generally refers to any neoplastic disorder, including such cellular disorders as, for example, brain cancer, glioblasoma multiforme (GBM), renal cell cancer, Kaposi's sarcoma, chronic leukemia, breast cancer, sarcoma, ovarian carcinoma, rectal cancer, throat cancer, melanoma, colon cancer, bladder cancer, mastocytoma, lung cancer and gastrointestinal or stomach cancer.

Metastasis is the final and often fatal step in the progression of breast cancer. Currently available therapeutic strategies at this stage of cancer progression are often non-specific, have only marginal efficacy and are highly toxic. This is in part due to the lack of knowledge about the molecular mechanisms regulating the development of aggressive cancers. Therapeutic approaches targeting only specific mechanisms involved in the development of aggressive breast cancers are urgently need. The expectation would be that this strategy would reduce unwanted toxicities associated with the therapy itself.

"Metastasis" generally refers to a multi-step process by which aggressive cancer cells spread out of the primary tissue and into other tissues of the body. Aggressive cancer cells that are nourished through angiogenesis, can migrate out of the primary tissue, and invade into the blood stream. These migratory aggressive cancer cells can remain vital by escaping the immune response, and consequently evade the blood stream and invade other tissues of the body. These cells can then proliferate to create secondary tumors.

Human GBMs are highly heterogeneous and vary in their response to therapeutic treatments. This disclosure describes how this heterogeneity is reflected in the response of multiple aggressive GBM cancers cell lines to the antiproliferative activity of synthetic and naturally occurring cannabinoids. Additionally, this disclosure discusses other constituents of marijuana that modulate the ability $\Delta^9$-THC to inhibit GBM cell growth and induce apoptosis. The disclosure demonstrates that the addition of CBD to $\Delta^9$-THC improves the overall potency and efficacy of $\Delta^9$-THC in the treatment of cancer.

In general, provided herein are methods for treating cancer by administering to a subject in need of such treatment a therapeutically effective amount of a composition consisting essentially of a combination of the cannabinoids cannabidiol (CBD) and tetrahydrocannabinol (THC). The methods include using a pharmaceutical composition that includes a combination of the cannabinoids cannabidiol (CBD) and tetrahydrocannabinol (THC).

A subject generally refers to mammals such as human patients and non-human primates, as well as experimental animals such as rabbits, rats, and mice, and other animals. Animals include all vertebrates, e.g., mammals and non-mammals, such as sheep, dogs, cows, chickens, amphibians, and reptiles.

"Treating" or "treatment" includes the administration of the compositions, compounds or agents of the invention to prevent or delay the onset of the symptoms, complications, or biochemical indicia of a disease, alleviating or ameliorating the symptoms or arresting or inhibiting further development of the disease, condition, or disorder (e.g., a disease or condition that is a result of immune system over-activation). "Treating" further refers to any indicia of success in the treatment or amelioration or prevention of the disease, condition, or disorder, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the disclosure to prevent or delay, to alleviate, or to arrest or inhibit development of the symptoms or conditions associated with cell proliferation, cancer and metastasis. The term "therapeutic effect" refers to the reduction, elimination, or prevention of the disease, symptoms of the disease, or side effects of the disease in the subject. "Treating" or "treatment" using the methods of the invention includes preventing the onset of symptoms in a subject that can be at increased risk of immune system over-activation but does not yet experience or exhibit symptoms, inhibiting the symptoms of immune system over-activation (slowing or arresting its development), providing relief from the symptoms or side-effects of the condition, and relieving the symptoms of the condition (causing regression). Treatment can be prophylactic (to prevent or delay the onset of the disease, or to prevent the manifestation of clinical or subclinical symptoms thereof) or therapeutic suppression or alleviation of symptoms after the manifestation of the disease or condition.

The disclosure also provides methods for screening and developing a library of Id-1 inhibitors comprising derivatizing a compound of Formula I, wherein the R group is modified. High throughput screening methodologies are particularly envisioned for the detection of modulators of expression of a target Id helix-loop-helix polypeptide, such as Id-1, described herein. Such high throughput screening methods typically involve providing a combinatorial chemical or peptide library containing a large number of potential therapeutic compounds (e.g., modulator compounds). Such combinatorial chemical libraries or ligand libraries are then screened in one or more assays to identify those library members (e.g., particular chemical species or subclasses) that display a desired characteristic activity. The compounds so identified can serve as conventional lead compounds, or can themselves be used as potential or actual therapeutics.

A combinatorial chemical library is a collection of diverse chemical compounds generated either by chemical synthesis or biological synthesis, by combining a number of chemical building blocks (i.e., reagents such as amino acids). As an example, a linear combinatorial library, e.g., a polypeptide or peptide library, is formed by combining a set of chemical building blocks in every possible way for a given compound length (i.e., the number of amino acids in a polypeptide or peptide compound). Millions of chemical compounds can be synthesized through such combinatorial mixing of chemical building blocks.

The preparation and screening of combinatorial chemical libraries is well known to those having skill in the pertinent art. Combinatorial libraries include, without limitation, peptide libraries (e.g. U.S. Pat. No. 5,010,175; Furka, 1991, Int. J. Pept. Prot. Res., 37:487-493; and Houghton et al., 1991, Nature, 354:84-88). Other chemistries for generating chemical diversity libraries can also be used. Nonlimiting examples of chemical diversity library chemistries include, peptoids (PCT Publication No. WO 91/019735), encoded peptides (PCT Publication No. WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., 1993, Proc. Natl. Acad. Sci. USA, 90:6909-6913), vinylogous polypeptides (Hagihara et al., 1992, J. Amer. Chem. Soc., 114:6568), nonpeptidal peptidomimetics with glucose scaffolding (Hirschmann et al., 1992, J. Amer. Chem. Soc., 114:9217-9218), analogous organic synthesis of small compound libraries (Chen et al., 1994, J. Amer. Chem. Soc., 116:2661), oligocarbamates (Cho et al., 1993, Science, 261:1303), and/or peptidyl phosphonates (Campbell et al., 1994, J. Org. Chem., 59:658), nucleic acid libraries (see Ausubel, Berger and Sambrook, all supra), peptide nucleic acid libraries (U.S. Pat. No. 5,539,083), antibody libraries (e.g., Vaughn et al., 1996, Nature Biotechnology, 14(3):309-314) and PCT/US96/10287), carbohydrate libraries (e.g., Liang et al., 1996, Science, 274-1520-1522) and U.S. Pat. No. 5,593,853), small organic molecule libraries (e.g., benzodiazepines, Baum C&EN, Jan. 18, 1993, page 33; and U.S. Pat. No. 5,288,514; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and the like).

EXAMPLES

Cell Culture and Treatments

Human breast cancer cells lines MDA-MB231 and MDA-MB436 obtained from the ATCC were used. To prepare the MDA-MB231-Id-1 cells, cells were infected with a pLXSN-Id-1 sense expression vector. In all experiments, the different cell populations were first cultured in RPMI media containing 10% fetal bovine serum (FBS). On the first day of treatment the media was replaced with vehicle control or drug in RPMI and 0.1% FBS. The media with the appropriate compounds were replaced every 24 h. $\Delta^9$-THC, CBN, CBD, CBG, and CP55,940 were obtained from NIH through the National Institute of Drug Abuse. WIN55,212-2 was purchased from Sigma/RBI (St. Louis, Mo.).

MTT Assay:

To quantify cell proliferation the MTT assay was used (Chemicon, Temecula, Calif.). Cells were seeded in 96 well plates. Upon completion of the drug treatments, cells were incubated at 37° C. with MTT for 4 h, and then isopropanol with 0.04 N HCl was added and the absorbance was read after 1 h in a plate reader with a test wavelength of 570 nm. The absorbance of the media alone at 570 nm was subtracted, and % control was calculated as the absorbance of the treated cells/control cells×100.

Boyden Chamber Invasion Assay:

assays were performed in modified Boyden Chambers (BD Biosciences, San Diego, Calif.). Cells at $1.5 \times 10^4$ per well were added to the upper chamber in 500 µl of serum-free medium supplemented with insulin (5 ng/ml). The lower chamber was filled with 500 µl of conditioned medium from fibroblasts. After a 20 h incubation, cells were fixed and stained. Cells that remained in the Matrigel or attached to the upper side of the filter were removed with cotton tips. Invasive breast cancer cells on the lower side of the filter were counted using a light microscope.

Quantitative Western Analysis:

Proteins were separated by SDS/PAGE, blotted on Immobilon membrane, and probed with anti-Id-1 and the appropriate secondary antibody. Band intensity values were obtained directly from the blot using AlphaeaseFC software (San Leandro, Calif.) or from film using Image-J (NIH, MD). As a normalization control for loading, blots were stripped and re-probed with mouse alpha-tubulin (Abeam, Cambridge, Mass.).

Polymerase Chain Reaction:

Total cellular RNA was isolated from breast cancer cells treated with vehicle control or with CBD. Transcripts for Id-1 and for ß-actin were reverse transcribed using SuperscriptII Reverse TranscriptaseII (Gibco-BRL), and polymerase chain reaction performed. The 5' and 3' PCR primers were AGGTGGTGCGCTGTCTGTCT (SEQ ID NO:1) and TAATTCCTCTTGCCCCCTGG (SEQ ID NO:2) for Id-1; and GCGGGAAATCGTGCGTGACATT (SEQ ID NO:3) and GATGGAGTTGAAGGTAGTTTCGTG (SEQ ID NO:4) for ß-actin. PCR was performed in buffer containing 1 µM of each of the 5' and 3' PCR primer and 0.5 U of Taq polymerase using 25 cycles for amplification of Id-1 and ß-actin cDNAs. The cycle conditions were 45 sec denaturation at 94° C., 45 sec annealing at 55° C., and 1 min extension at 72° C.

Id-1 Promoter Reporter Assays:

A SacI-BspHI fragment of 2.2 kb corresponding to the 5' upstream region of human Id-1 gene and driving a luciferase gene in a PGL-3 vector (Promega) has already been described (Id-1-sbsluc). Cells were plated in six well dishes in medium supplemented with 10% FBS and 5 µg/ml insulin. After 24 h, cells were cotransfected with 6 µg of luciferase reporter plasmids and 2 µg of pCMVβ (Clontech) using superfect reagent (Qiagen). pCMVβ contained bacterial β-galactosidase and served to control for variation in transfection efficiency. 3 h after transfection, the cells were rinsed twice with PBS and were cultured in the absence or presence of CBD for 48-72 h. Cell pellets were lysed in 80 µl of reporter lysis buffer (Promega) for 10 min at room temperature. Lysed cells were centrifuged and supernatants harvested. Luciferase and β-gal assays were performed using Luciferase Assay System (Promega), β-Gal Assay Kit (Clontech) and a 2010 luminometer (Pharmingen).

Statistical Analysis:

The $IC_{50}$ values with corresponding 95% confidence limits were compared by analysis of logged data (GraphPad Prism, San Diego, Calif.). When just the confidence limits of the $IC_{50}$ values overlapped significant differences were determined using unpaired Student's t-test. Significant differences were also determined (Prism) using ANOVA or the unpaired Student's t-test, where suitable. Bonferroni-Dunn post-hoc analyses were conducted when appropriate. P values <0.05 defined statistical significance.

The ability of CBD to regulate the expression of key genes that control breast cancer cell aggressiveness and invasiveness was determined. A potential candidate protein that could mediate the effects of CBD on both phenotypes was the helix-loop-helix protein Id-1. It was determined that treatment of MDA-MB231 cells with CBD led to a concentration-dependent inhibition of Id-1 protein expression (FIG. 1, panel B and panel C). The inhibitory effect of CBD on Id-1 expression occurred at concentrations as low as 100 nM. CBD was more effective at reducing Id-1 protein expression compared to other cannabinoid compounds (FIG. 1, panel C). The CBD concentrations effective at inhibiting Id-1 expression correlated with those used to inhibit the proliferative and invasive phenotype of MDA-MB231 cells. Furthermore, the time period needed to observe the down-regulation of Id-1 protein in the presence of CBD correlated with the inhibitory effects of CBD on the aggressiveness and invasiveness of MDA-MB231 cells (FIG. 1, panel D).

The ability of CBD to modulate Id-1 gene expression was determined Referring to FIG. 2, panel A, Id-1 mRNA expression was significantly reduced upon treatment with CBD. To determine if this effect was due to the inhibition of transcription, a construct was used that contained the Id-1 promoter fused to a luciferase reporter in a PGL-3 basic vector. This construct was transiently transfected into MDA-MB231 cells. Twenty-four hours after transfection, MDA-MB231-Id-1-luc cells were treated with CBD for 2 or 3 days and luciferase activity was measured (FIG. 2, panel B and panel C). Transfection efficiency and analysis of equal amounts of total protein were controlled by contransfection of the cells with pCMVB containing ß-galactosidase. Treatment with CBD resulted in a significant inhibition of luciferase activity. This effect was time-dependent with the greatest inhibition occurring on day 3. These findings correlated to the data obtained when the expression of the Id-1 protein was assessed by Western analysis.

To determine if Id-1 represented a key mediator of CBD effects in highly aggressive breast cancer cells, Id-1 was constitutively expressed into MDA-MB231 cells (+Id1 as described in FIG. 7). The ectopic Id-1 gene, which is not under the control of the endogenous promoter, was introduced in the cells using the pLXSN retroviral vector. As a control, cells were infected with an empty pLXSN vector (−Id1). In control cells, treatment with CBD led to a significant reduction in cell invasiveness (FIG. 7, panel A (upper panels) and FIG. 7, panel B). Western blotting confirmed the down-regulation of Id-1 expression in this control cell line (FIG. 7, panel C). In contrast to these results, CBD did not inhibit cell invasiveness (FIG. 7, panel A (lower panels) and FIG. 7, panel B) or Id-1 expression (FIG. 7, panel C) in MDA-MB231+Id1 cells that ectopically expressed Id-1.

Invasion is also an important step towards brain cancer progression. The disclosure also provide methods and compositions for the treatment of brain cancer progression. Therefore, the ability of CBD to reduce the growth and invasiveness activity of glioblastoma muliforme (GBM) cancer cells was tested. Multiple glioblastoma muliforme (GBM) cell lines were treated for three days and $IC_{50}$ values were calculated and provided in Table 2 below:

| Cell Line | CBD $IC_{50}$ |
|---|---|
| SF126 | 1.2 (1.1-1.3) |
| U87 | 0.7 (0.5-1.0) |
| U251 | 0.6 (0.5-0.7) |

$IC_{50}$ values for the antiproliferative effects of CBD were calculated in multiple GBM cell lines over a three day treatment. Cell proliferation was assessed using the MTT assay. Data are the means and corresponding 95% confidence limits of at least three experiments. $IC_{50}$ values are reported in μM.

It was determined that U251 cells were the most sensitive to the antiproliferative activity of CBD. CBD was also able to significantly reduce the invasiveness of U251 cells (FIG. 10).

It was determined that treatment of U251 cells with CBD led to a concentration-dependent inhibition of Id-1 protein expression (FIG. 11).

In order to determine the SAR between cannabinoids and the inhibition of Id-1, MDA-MB231 cells were treated for two days with multiple cannabinoid compounds and Id-1 protein levels were assessed. The compounds used included: 1) Agonists and antagonists to the putative abnormal (Abn)-CBD receptor, Abn-CBD and 01602; 2) a synthetic cannabinoid analog that has high affinity for $CB_1$ and $CB_2$ receptors, CP55,940; 3) natural *cannabis* constituents that have appreciable affinity for $CB_1$ and $CB_2$ receptors, $\Delta^9$-THC and CBN (Pertwee, 1997; Jarai et al., 1999). The greatest inhibition of Id-1 was observed in the presence of CBD. Also a small inhibition of Id-1 was observed in the presence of CP55, 940. No inhibition of Id-1 was observed in the presence of $\Delta^9$-THC, 0-1602 and Abn-CBD.

The data demonstrates that cannabidiol (CBD) is an effective inhibitor of Id-1. The inhibition of Id-1 does not appear to be related to the putative Abn-CBD receptor. It also appears that the opened tetrahydropyran ring in CBD is only partially responsible for its activity, since Abn-CBD and 0-1602 did not inhibit Id-1. One potential key structure is the classical cannabinoid aliphatic side chain: a region crucial for the activity of numerous classical and synthetic cannabinoids. CP55,940 and CBN can partially inhibit Id-1. In comparison to the classical cannabinoid structure ($\Delta^9$-THC), each compound contains the side chain region, and the cyclohexyl ring, however, the pyrane ring is removed in CP55,940. CP55,940 has an opened tetrahydropyran ring similar to CBD. The data suggests that a general structural component of CBD, responsible for Id-1 inhibition, is the combination of the opened tetrahydropyran ring and the classical cannabinoid aliphatic side chain.

Cell Culture and Treatments:

The human GBM cell lines used were SF126, U87 and U251. Cell lines were maintained at 37° C. and 5% $CO_2$. In all experiments, the different cell populations were first cultured in RPMI media containing 10% fetal bovine serum (FBS). On the first day of treatment the media was replaced with vehicle control or drug in RPMI and 0.1% FBS. The media with the appropriate compounds were replaced every 24 h. $\Delta^9$-THC, CBN, CBD, CBG, and CP55,940 were obtained from NIH through the National Institute of Drug Abuse. WIN55,212-2 was purchased from Sigma/RBI (St. Louis, Mo.).

MTT Assay:

To quantify cell proliferation the 3-[4,5-dimethylthiazol-2-yl]-2,5-diphenyl tetrasodium bromide (MTT) assay was used (Chemicon, Temecula, Calif.). Cells were seeded in 96 well plates at $1\times10^3$ cells/well for seven day experiments and $3\times10^3$ cells per $cm^2$ for three day experiments to obtain optimal cell density throughout the experiment. Cells were incubated at 37° C. with MTT for four hours, and then isopropanol with 0.04 N HCl was added and the absorbance was read after one hour in a plate reader with a test wavelength of 570 nm. The absorbance of the media alone at 570 nm was subtracted, and % control was calculated as the absorbance of the treated cells/control cells×100.

Apoptosis:

Cells were grown in 6 well culture dishes and were treated with the appropriate compounds every 24 hours for three days. The cells were trypsinized, washed with PBS, and processed for labeling with fluorescein-tagged UTP nucleotide and PI by use of an Apo-Direct apoptosis kit obtained from Phoenix Flow Systems (San Diego, Calif.) and was used according to the manufacturer's protocol. The labeled cells were analyzed by flow cytometry. Cell Flow Cytometry in combination with PI and annexin staining was used to quantify the percentage of cells undergoing apoptosis in control and treatment groups. % control was calculated as annexin positive staining in treated cells/control cells×100. PI staining was used to distinguish necrotic cells from those undergoing apoptosis.

Quantitative Western Analysis:

Cells cultured and treated in 6-well dishes were washed twice with cold PBS. Lysis buffer was added and cells lysed by freezing for 10 min at −70° C. and then thawing. Cell lysate was collected and the concentration was determined using Bradford reagent. Equal amounts of protein were heated to 90° C. in Laemmli sample buffer with β-mercaptoethanol, and loaded onto a precast SDS-PAGE gel (Bio-Rad Laboratories, Hercules, Calif.). Protein was transferred to an Immobilon membrane (Millipore, Billerica, Mass.) overnight at 2-4° C. Blots were then blocked with 5% nonfat dry milk in TBS+Tween for 1 h. Primary antibody from Millipore (rabbit anti-phospho-JNK, rabbit anti-phospho-p38, rabbit anti-phospho-ERK1/2 and rabbit anti-ERK1/2, 1 mcg/mL) in blocking buffer was then added for 1 h. The blots were then rinsed three times 10 min with TBS+Tween. Secondary antibody (Donkey Anti-Rabbit IgG, Jackson Immunoresearch, West Grove, Pa.) was then added. Blots were incubated for 45 min and then washed 4 times for 15 min each. The blots were developed with SuperSignal Femto (Pierce, Rockford, Ill.), and imaged on either a Fluorchem 8900 (Alpha Innotech, San Leandro, Calif.) or ECL Hyperfilm (Amersham-Pharmacia, Piscataway, N.J.). Band intensity values were obtained (after background subtraction)

directly from the Fluorchem 800 using AlphaeaseFC software (San Leandro, Calif.) or from film using Image-J (NIH, MD). As a normalization control for loading, blots were stripped and re-probed with mouse alpha-tubulin (Abcam, Cambridge, Mass.) and goat anti-mouse IgG (Jackson Immunoresearch) for the primary and secondary antibodies, respectively.

Cell Cycle Analysis.

U251 cells were grown in Petri dishes (100 mm×15 mm) and received drug treatments for 2 days. On the third day, the cells were harvested and centrifuged at 1200 rpm for 5 minutes. The pellet was washed 1× with PBS+1% BSA, and centrifuged again. The pellet was resuspended in 0.5 ml of 2% paraformaldehyde (diluted with PBS) and left to fix overnight at room temperature. The next day the cells were pelleted and resuspended in 0.5 ml 0.3% Triton in PBS and incubated for 5 minutes at room temperature. The cells were then washed 2 times with PBS+1% BSA. The cells were finally suspended in PBS (0.1% BSA) with 10 ug/ml Propidium Iodide and 100 µg/ml RNAse. The cells were incubated for 30 minutes at room temperature before being stored at 4 C. Cell cycle was measured using a FACS Calibur using Cell Quest Pro and Modfit software.

Radical Oxygen Species (ROS) Measurements.

The production of cellular radical oxygen species (ROS)/$H_2O_2$ was measured using 2'-7'Dichlorodihydrofluorescein (DCFH-DA, Sigma Aldrich). DCFH-DA is deacylated intracelluarlly into a non-fluorescent product, which reacts with intracellular ROS to produce 2'-7'Dichlorofluorescein. 2'-7'Dichlorofluorescein remains trapped inside the cell, and can be measured quantitatively. U251 cells were plated onto 6 well dishes and received drug treatments for three days. On the third day, 2 µM DCFH-DA was added to the media (MEM with 0.1% FBS) and the cells were incubated with DCFH-DA overnight. The next day, the cells were trypsinized, washed with PBS, and the fluorescent intensity was measured using a FACS and cell quest pro software.

Statistical analysis: Treatment groups were divided into 1) no treatment (control), 2) $\Delta^9$-THC alone, 3) CBD alone, 4) $\Delta^9$-THC and CBD combined. Positive and negative aspects of constituent interaction were determined in this 2×2 design using 2-way analysis of variance as described by (Slinker, 1998). In the proliferation assays, $IC_{50}$ values with corresponding 95% confidence limits were calculated using non-linear analysis of logged data (GraphPad Prism, San Diego, Calif.). Significant differences were also determined using ANOVA where suitable. Bonferroni-Dunn post-hoc analyses were conducted when appropriate. P values <0.05 defined statistical significance.

Two commonly used $CB_1$ and $CB_2$ receptors agonists were chosen to study the effect of cannabinoid treatment on the growth of three human glioblastoma multiforme (GBM) cell lines. $\Delta^9$-THC, a natural *cannabis* constituent, and WIN 55,212-2, a synthetic cannabinoid analog, have high affinity for $CB_1$ and $CB_2$ receptors. Human GBM cells were treated with multiple concentrations of $\Delta^9$-THC and WIN 55,212-2. Cell proliferation was measured using the MTT assay and corresponding $IC_{50}$ values were calculated (Table 3). SF126 cells overall were most sensitive to the antiproliferative effects of $\Delta^9$-THC and WIN 55,212-2. Cannabidiol (CBD), a natural *cannabis* compound that does not have appreciable affinity for $CB_1$ and $CB_2$ receptors, was also tested in the GBM cell line, SF126. The $IC_{50}$ value was 0.73 µM (0.64-0.82).

TABLE 3

$\Delta^9$-THC and WIN 55,212-2 inhibit cell proliferation in GBM cell lines.

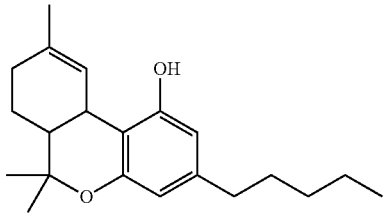

| | $\Delta^9$-THC $IC_{50}$ | WIN 55,212-2 $IC_{50}$ |
|---|---|---|
| SF126 | 0.9 (0.7-1.4) | 0.84 (0.74-0.95) |
| U87 | 1.6 (1.0-2.4) | 0.77 (0.65-0.90) |
| U251 | 1.1 (0.84-1.4) | 1.1 (0.97-1.3) |

$IC_{50}$ values for the antiproliferative effects of $\Delta^9$-THC and WIN 55,212-2 were calculated in three GBM cell lines over a seven day treatment. Cell proliferation was assessed using the MTT assay. Data are the means and corresponding 95% confidence limits of at least three experiments. $IC_{50}$ values are reported in µM.

Three groups of cannabinoid compounds were chosen for a broader analysis of antiproliferative activity in the single GBM cell line, SF126 (Table 4). 1) Natural *cannabis* constituents that have affinity for $CB_1$ and $CB_2$ receptors, $\Delta^9$-THC and CBN. 2) Synthetic cannabinoid analogs that have high affinity for $CB_1$ and $CB_2$ receptors, WIN 55,212-2 and CP55,940. 3) Natural *cannabis* constituents that do not have appreciable affinity for $CB_1$ and $CB_2$ receptors, CBD and CBG.

TABLE 4
Multiple classes of cannabinoids inhibit SF126 cell proliferation.
| | Compound | SF126 |
|---|---|---|
| 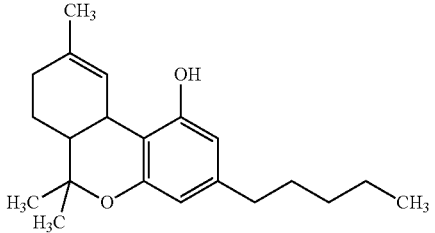 [SMILES: CCCCCc1cc(O)c2c(c1)OC(C)(C)C1CCC(C)=CC21] | Δ⁹-THC | 2.5 (1.8-3.4) |
| 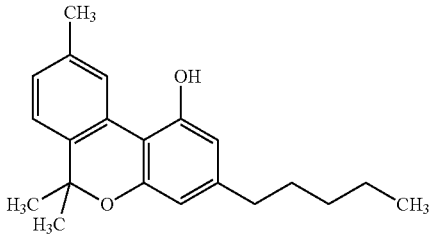 [SMILES: CCCCCc1cc(O)c2c(c1)OC(C)(C)c1ccc(C)cc1-2] | CBN | 1.2 (0.9-1.6) |
| 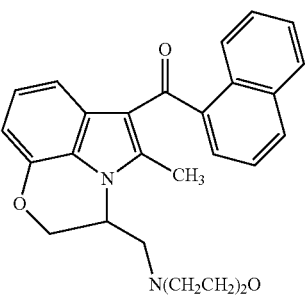 | WIN55, 212-2 | 1.3 (1.2-1.4) |
| 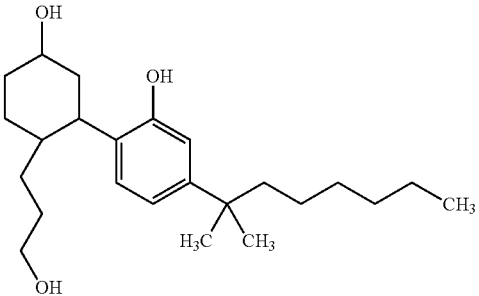 [SMILES: CCCCCCC(C)(C)c1ccc(C2CC(O)CCC2CCCO)c(O)c1] | CP 55, 940 | 3.3 (2.9-3.7) |
| 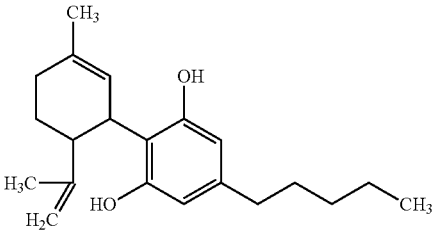 [SMILES: C=C(C)C1CCC(C)=CC1c1c(O)cc(CCCCC)cc1O] | CBD | 1.2 (1.1-1.3) |

TABLE 4-continued

Multiple classes of cannabinoids inhibit SF126 cell proliferation.

| Compound | SF126 |
|---|---|
| CBG | 1.6 (1.5-1.7) |

IC$_{50}$ values for the antiproliferative effects of cannabinoid agonists on SF126 cell growth over a three day treatment were obtained. Cell proliferation was assessed using the MTT assay. Data are the means and corresponding 95% confidence limits of at least three experiments. IC$_{50}$ values are reported in µM.

Treatment periods were shortened to three days during experiments with additional agonists since significant effect were observed at this time point. SF126 cells were treated with a range of concentrations of multiple cannabinoid agonists, and the corresponding IC$_{50}$ values were calculated. The rank order of potencies was: CBD=CBN=WIN 55,212-2>CBG>$\Delta^9$-THC=CP55940. Again, CBD was one of the most potent compounds tested.

$\Delta^9$-THC and CBD act synergistically to inhibit the growth of multiple GBM cell lines. The CB$_1$ and CB$_2$ receptor agonist, $\Delta^9$-THC, can inhibit GBM growth in vitro and in vivo and is currently being used in a pilot clinical trial (Velasco et al., 2007). CBD, a cannabinoid constituent with negligible affinity for CB$_1$ and CB$_2$ receptors can also inhibit the growth of GBM in vitro and in vivo (Massi et al., 2004; Massi et al., 2008). The data provided herein determined that of several non-psychoactive cannabinoids tested, CBD was overall the most potent inhibitor of GBM cell growth. The positive and negative aspects of constituent interaction were tested by analyzing the activity of different concentration combinations of $\Delta^9$-THC and CBD in a 2×2 design (FIG. 3). When applied in combination, $\Delta^9$-THC and CBD produced synergistic inhibition of cell growth in SF126 and U251 cells but not in U87 cells (FIG. 3 A, B, C). Concentrations of $\Delta^9$-THC and CBD alone that produce only minimal effects on cell proliferation were again combined and further tested in a 2×2 factorial design in the positive responding cell lines (SF126 and U251) (FIG. 3 D, E, F). The most pronounced synergistic activity was observed with U251 cells. Therefore, this cell line was used in the remainder of the experiments.

In addition to uncontrolled cell growth, a hallmark phenotype of aggressive GBM tumor cells is their ability to migrate away for the primary tumor of origin and invade into neighboring CNS tissue. Experiments were performed to determine whether the addition of CBD to $\Delta^9$-THC would improve the activity of the compound to inhibit migration and invasion through a reconstituted basement membrane in a Boyden chamber. $\Delta^9$-THC effectively inhibited the invasiveness of U251 cells. Additionally, $\Delta^9$-THC was significantly more potent at inhibiting U251 cell invasiveness in comparison to the inhibition of cell growth and induction of apoptosis. The predicted IC$_{50}$ for the ability of $\Delta^9$-THC to inhibit U251 cell invasiveness was 85 nM (49-150). Whereas both THC and CBD were able to inhibit U251 cell invasiveness, the combined addition of the compounds did not result in activity suggesting a synergistic interaction.

Since $\Delta^9$-THC and CBD acted synergistically to inhibit GBM growth but not invasiveness, experiments were focused on the antiproliferative activity of the combination treatment. The highly active 4:1 (1.7 µM: 0.4 µM) ratio of $\Delta^9$-THC and CBD (FIGS. 3E and F) was used as the standard combination treatment for the remainder of the experiments.

The combination treatment of $\Delta^9$-THC and CBD leads to the modulation of specific mitogen activated kinases (MAPK). The regulation of ERK, JNK, and p38 MAPK activity plays a role in controlling cell growth and apoptosis. U251 cells were used to determine whether modulation of ERK, JNK, and p38 MAPK activity occurred. Treatment with the combination of cannabinoids led to a profound down-regulation of p-ERK but produced no significant change in total ERK (FIG. 4A). Additionally, no inhibition of JNK or p38 MAPK activity was observed (FIG. 4B). When U251 cells were treated with individual concentration of $\Delta^9$-THC and CBD, instead of the combination, no changes in pERK were observed (FIG. 4C).

The combination treatment of $\Delta^9$-THC and CBD inhibits cell cycle. The large reduction in GBM cell growth and ERK activity, observed in the presence of the combination treatment of $\Delta^9$-THC and CBD, suggested there would be a corresponding modulation of the cell cycle and programmed cell death. Therefore, U251 cells were treated with $\Delta^9$-THC and CBD alone or with the combination of the two, and cell cycle was analyzed using cell flow cytometry (FIG. 8). The combination of $\Delta^9$-THC and CBD produces an increase in the population of cells in G1 phase and a decrease in cells in S phase. Additionally, there was an increase in the population of cells in the G2/M phase. These changes in G1, S and G2/M phase are hallmarks of cell cycle arrest. When administered separately, 1.7 µM of $\Delta^9$-THC and 0.4 µM CBD both produced increases in the population of cells in G1 and G2/M phase and decreases in cells in S phase. Albeit, the magnitude of these effects was reduced compared to those observed with the combination treatment.

Next apoptosis was measured using cell flow cytometry. When $\Delta^9$-THC and CBD were combined a large increase in apoptosis was observed (FIG. 5). Separately 1.7 µM $\Delta^9$-THC and 0.4 µM CBD did not produce significant changes in apoptosis.

Apoptosis produced by the combination of $\Delta^9$-THC and CBD was partially blocked by the CB$_2$ receptor antagonist, SR144528, but complete reversal was observed in the presence of the anti-oxidant, α-tocopherol (TCP) (FIG. 6A). The concentrations of the individual cannabinoids ($\Delta^9$-THC and CBD) were next increased in order to attempt to match levels of apoptosis produced by the combination treatment. The purpose of these experiments was to determine whether the compounds alone recruited similar pathways as compared to the combination of $\Delta^9$-THC and CBD. When U251 cells were treated with $\Delta^9$-THC alone, the induction of apoptosis was completely blocked by α-tocopherol and partially blocked by the CB2 antagonist, SR144528 (FIG. 6B). However, $\Delta^9$-THC alone could not produce the level of apoptosis observed with the combination treatment (FIG. 6A and FIG. 6B). This finding was not simply an issue of the treatment concentration used since continuing to increase levels of $\Delta^9$-THC did not produce a greater induction of apoptosis. When U251 cells were treated with CBD alone, the induction of apoptosis was completely blocked by α-tocopherol but no reversal was observed with SR144528 (FIG. 6C); this result would be expected since CBD does not interact efficiently with either $CB_1$ or $CB_2$ receptors.

The ability of the higher concentrations of $\Delta^9$-THC and CBD alone to inhibit p-ERK were also studied and compared to the combination treatment (FIG. 6D). Again, the combination treatment produced a profound down regulation of p-ERK. However, the higher concentration of $\Delta^9$-THC alone had no effect on p-ERK activity. The higher concentration of CBD produced a small inhibition of p-ERK. This suggests the pathway (s) activated by the $\Delta^9$-THC and CBD combination that leads to p-ERK down-regulation, is unique to the combination treatment. As predicted by α-tocopherol blockade, the combination of $\Delta^9$-THC and CBD produced a significant increase in the formation of ROS as assessed by DCDHF-DA oxidation (FIG. 6E).

The combination treatment of $\Delta^9$-THC and CBD produces the activation of multiple caspases. Caspases play a primary role in the regulation of programmed cell death. Therefore, multiple caspase pathways were evaluated to determine mechanisms by which the combination treatment increased apoptosis (FIG. 9). Treatment with the combination of $\Delta^9$-THC and CBD led to a significant up-regulation of caspase 3, 7, and 9 activities as well as an increase in PARP. Small increases in the activity of caspase 7, caspase 9 and PARP but not caspase 3 were observed when U251 cells were treated with the individual concentration of $\Delta^9$-THC. In the presence of CBD alone no changes in caspase activity were observed.

A wide range of cannabinoids inhibit the proliferation of human GBM cells. In addition to testing $\Delta^9$-THC, the analysis included the non-psychoactive *cannabis* constituents CBD, CBN and CBG. Overall, CBD was the most potent inhibitor tested.

Combining $\Delta^9$-THC and CBD together resulted in a synergistic increase in the inhibition GBM growth and produced significant increases in apoptosis. This synergistic activity occurred in two of three GBM cell lines tested. The synergistic inhibition of GBM cell growth was in part the result of a greater amount of apoptosis being produced in presence of the combination compared to administration of $\Delta^9$-THC alone. Treatment of U251 cells with the combination of cannabinoids led to a profound down-regulation of ERK activity, but not p38 MAPK and JNK1/2. The reduction of ERK activity was specific for the combination treatment indicating that all the effects observed were not simply due to an increase in potency of $\Delta^9$-THC upon co-application with CBD. The specific reduction in ERK activity, observed in the presence of the combination treatment, may be one of the primary mechanisms leading to the synergistic increase in inhibition of GBM cell growth and the induction of apoptosis. $\Delta^9$-THC was also effective at inhibiting the invasiveness of U251 cells, however, there was no suggestion of a synergistic interaction upon addition of CBD.

An increase in apoptosis produced by the combination of $\Delta^9$-THC/CBD was partially dependent on $CB_2$ receptor activation. Apoptosis produce by treatment of $\Delta^9$-THC alone was also partially dependent on $CB_2$ receptor activation. Importantly, the induction of apoptosis in the presence of the combination treatment was significantly greater than that observed with $\Delta^9$-THC alone. Apoptosis produced by CBD in U251 cells was not dependent $CB_2$ receptor activation. Comparable results with CBD were also observed using another GBM cell line, SF126 (data not shown). Apoptosis produced by the combination of $\Delta^9$-THC and CBD was greatly dependent on the production of oxidative stress and resulted in the activation of both extrinsic and extrinsic caspase pathways.

$\Delta^9$-THC and CBD activate unique pathways in GBM cells that ultimately culminate in inhibition of cancer cell growth and invasion as well as induction of cell death. The data presented here show that the synergistic activity of the combination treatment is due in part to a specific convergence of distinct pathways controlled by the individual compounds. This convergence of inhibitory pathways unique to $\Delta^9$-THC and CBD leads to an overall synergistic reduction of GBM cell growth and survival. Combinations, compared to individual drug treatments with specific cannabinoid-based compounds may represent a significant improvement for the treatment of patients with GBM. These synergistic effects may also be present in additional cancers. With the discovery of a specific molecular mechanism potentially explaining the synergistic effects, additional combination treatments may able to be refined in order to further improve antitumor activity.

The examples set forth above are provided to give those of ordinary skill in the art a complete disclosure and description of how to make and use the embodiments of the apparatus, systems and methods of the invention, and are not intended to limit the scope of what the inventors regard as their invention. Modifications of the above-described modes for carrying out the invention that are obvious to persons of skill in the art are intended to be within the scope of the following claims.

A number of embodiments of the invention have been described. Nevertheless, it will be understood that various modifications may be made without departing from the spirit and scope of the invention. Accordingly, other embodiments are within the scope of the following claims.

What is claimed is:

1. A method of treating glioblastoma multiforme in a human, consisting essentially of administering to said human in need of such treatment a therapeutically effective amount of a combination comprising a cannabidiol (CBD) and a tetrahydrocannabinol (THC).

2. The method of claim 1, wherein the treatment of the glioblastoma multiforme in a human in need thereof is to reduce cell growth.

* * * * *

SEQUENCE LISTING

<160> NUMBER OF SEQ ID NOS: 4

<210> SEQ ID NO 1
<211> LENGTH: 20
<212> TYPE: DNA
<213> ORGANISM: Artificial

```
<220> FEATURE:
<223> OTHER INFORMATION: 5' PCR primer Id-1 protein

<400> SEQUENCE: 1
aggtggtgcg ctgtctgtct                                              20

<210> SEQ ID NO 2
<211> LENGTH: 20
<212> TYPE: DNA
<213> ORGANISM: Artificial
<220> FEATURE:
<223> OTHER INFORMATION: 3' PCR primer Id-1 protein

<400> SEQUENCE: 2
taattcctct tgccccctgg                                              20

<210> SEQ ID NO 3
<211> LENGTH: 22
<212> TYPE: DNA
<213> ORGANISM: Artificial
<220> FEATURE:
<223> OTHER INFORMATION: 5' PCR primer beta-actin

<400> SEQUENCE: 3
gcgggaaatc gtgcgtgaca tt                                           22

<210> SEQ ID NO 4
<211> LENGTH: 24
<212> TYPE: DNA
<213> ORGANISM: Artificial
<220> FEATURE:
<223> OTHER INFORMATION: 3' PCR primer beta-actin

<400> SEQUENCE: 4
gatggagttg aaggtagttt cgtg                                         24
```